United States Patent
Cohen et al.

(10) Patent No.: US 6,426,043 B1
(45) Date of Patent: Jul. 30, 2002

(54) AUTOMATIC HANDLER FOR FEEDING CONTAINERS INTO AND OUT OF AN ANALYTICAL INSTRUMENT

(75) Inventors: Beri Cohen, Hartsdale; Thomas W. DeYoung, Stormville; Krunoslav Esteban Draganovic, Upper Nyack; Paul E. Purpura, Yorktown, all of NY (US)

(73) Assignee: Bayer Corporation, Tarrytown, NY (US)

( * ) Notice: Subject to any disclaimer, the term of this patent is extended or adjusted under 35 U.S.C. 154(b) by 0 days.

(21) Appl. No.: 09/503,918

(22) Filed: Feb. 15, 2000

Related U.S. Application Data

(62) Division of application No. 09/115,391, filed on Jul. 14, 1998, now Pat. No. 6,331,437.

(51) Int. Cl.[7] ................................................ G01N 35/04
(52) U.S. Cl. ......................... 422/63; 422/65; 422/104; 422/105; 422/106
(58) Field of Search .................... 422/63, 65, 100–104, 422/105, 106; 436/47, 48, 180, 43; 73/864.21, 864.24, 864.25; 198/473.1, 738, 740, 747, 748

(56) References Cited

U.S. PATENT DOCUMENTS

| | | |
|---|---|---|
| 3,575,692 A | 4/1971 | Gilford et al. |
| 3,897,216 A | 7/1975 | Jones |
| 3,923,463 A | 12/1975 | Bagshawe et al. |
| 3,955,436 A | 5/1976 | Tucker et al. |
| 3,977,794 A | 8/1976 | Liedholz |
| 4,007,013 A | 2/1977 | Kotacka |
| 4,022,579 A | 5/1977 | Revillet et al. |
| 4,165,484 A | 8/1979 | Haynes |
| 4,276,258 A | 6/1981 | Ginsberg |
| 4,276,260 A | 6/1981 | Drbal et al. |
| 4,303,611 A | 12/1981 | Jessop |
| 4,311,484 A | 1/1982 | Fosslien |
| 4,341,736 A | 7/1982 | Drbal et al. |
| 4,387,076 A | 6/1983 | Cabrera et al. |
| 4,475,411 A | 10/1984 | Wellerfors |
| 4,495,149 A | 1/1985 | Iwata et al. |
| 4,503,385 A | 3/1985 | Haynes |
| 4,534,465 A | 8/1985 | Rothermel et al. |
| 4,609,017 A | 9/1986 | Coulter et al. |
| 4,729,876 A | 3/1988 | Hennessy et al. |
| 4,752,690 A | 6/1988 | James |
| 4,756,201 A | 7/1988 | Uffenheimer |
| 4,799,393 A | 1/1989 | Uffenheimer |
| 4,811,611 A | 3/1989 | Uffenheimer |

(List continued on next page.)

FOREIGN PATENT DOCUMENTS

JP              63-85457       4/1988

OTHER PUBLICATIONS

Chem 1 User's Guide Section 3E6.1 (15 pp) Bayer Corporation, undated.

*Primary Examiner*—Joseph W. Drodge
(74) *Attorney, Agent, or Firm*—Andrew L. Klawitter; John M. Paolino

(57) ABSTRACT

A sample handler moves and positions racks, containing sample tubes, in an analytical instrument. The sample handler has an in-feed and out-feed that advance sample tube racks using a walking beam mechanism. The racks are seated within the in-feed and are transported onto a cross-feed. The racks and tubes contained thereon are moved past detection devices that identify the samples and measure various properties thereof. Thereafter, the cross-feed moves the racks to a position behind the out-feed where the walking beam mechanism moves the tube racks out of the analytical instrument.

4 Claims, 28 Drawing Sheets

U.S. PATENT DOCUMENTS

| | | | |
|---|---|---|---|
| 4,835,711 A | * | 5/1989 | Hutchins et al. |
| 5,040,890 A | | 8/1991 | North, Jr. |
| 5,167,926 A | | 12/1992 | Kirmura et al. |
| 5,186,339 A | | 2/1993 | Heissler |
| 5,207,986 A | | 5/1993 | Kadota et al. |
| 5,260,028 A | * | 11/1993 | Astle .................... 422/65 |
| 5,350,564 A | | 9/1994 | Mazza et al. |
| 5,417,922 A | | 5/1995 | Markin et al. |
| 5,419,871 A | | 5/1995 | Muszak et al. |
| 5,439,646 A | | 8/1995 | Tanimizu et al. |
| 5,529,166 A | | 6/1996 | Markin et al. |
| 5,589,137 A | | 12/1996 | Markin et al. |
| 5,623,415 A | | 4/1997 | O'Bryan et al. |
| 5,735,387 A | * | 4/1998 | Polaniec et al. ............ 422/65 |
| 5,800,780 A | | 9/1998 | Markin |
| 5,861,563 A | | 1/1999 | Boyd et al. |
| 5,880,364 A | * | 3/1999 | Dam .................... 73/290 V |
| 5,948,360 A | | 9/1999 | Rao et al. |
| 5,959,221 A | | 9/1999 | Boyd et al. |
| 6,293,750 B1 | * | 9/2001 | Cohen et al. |
| 6,331,437 B1 | * | 12/2001 | Cohen et al. ............ 436/43 |
| 6,347,552 B1 | * | 2/2002 | Purpura et al. |
| 6,358,472 B1 | * | 3/2002 | DeYoung et al. ........ 422/65 |

* cited by examiner

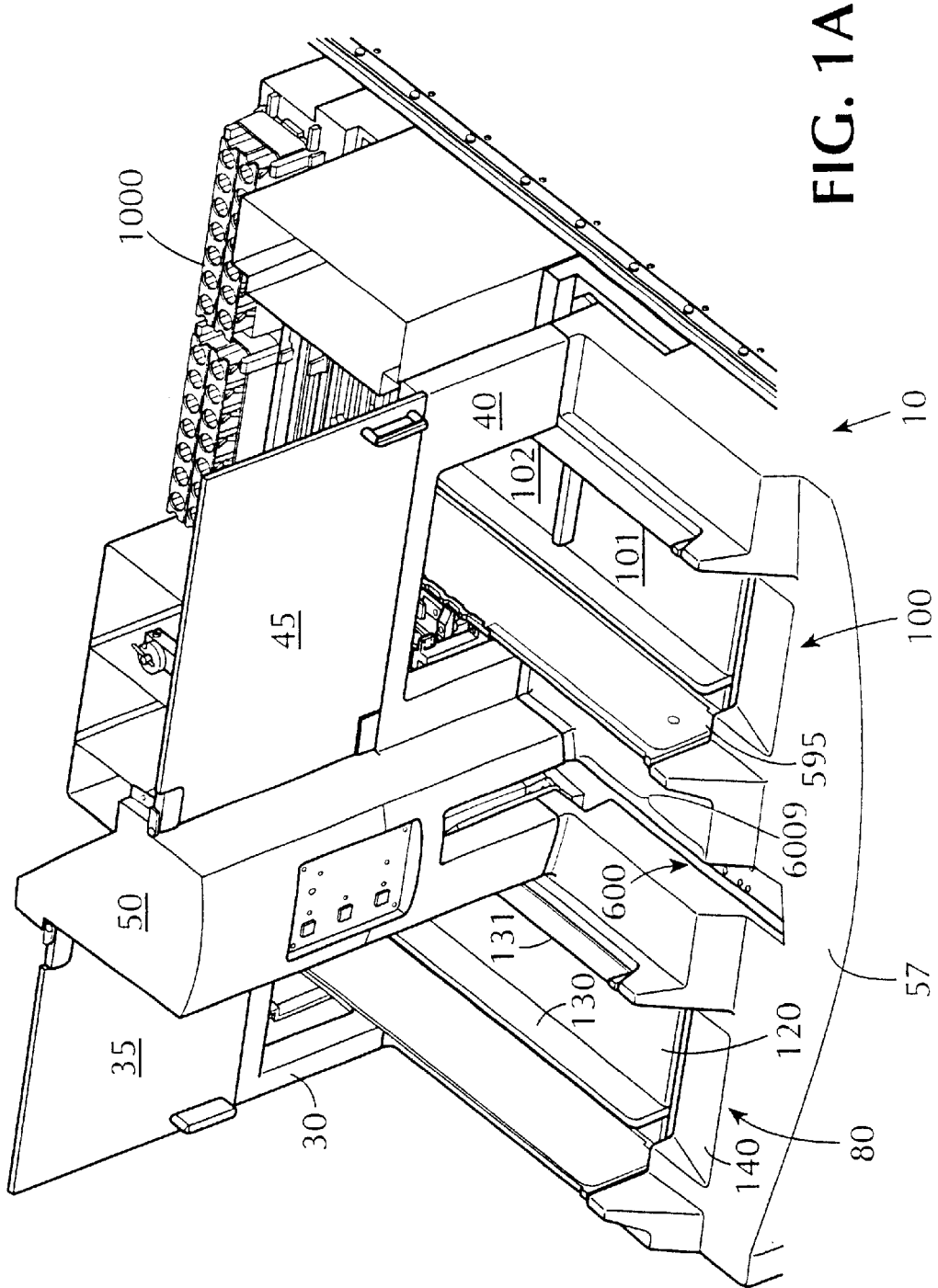

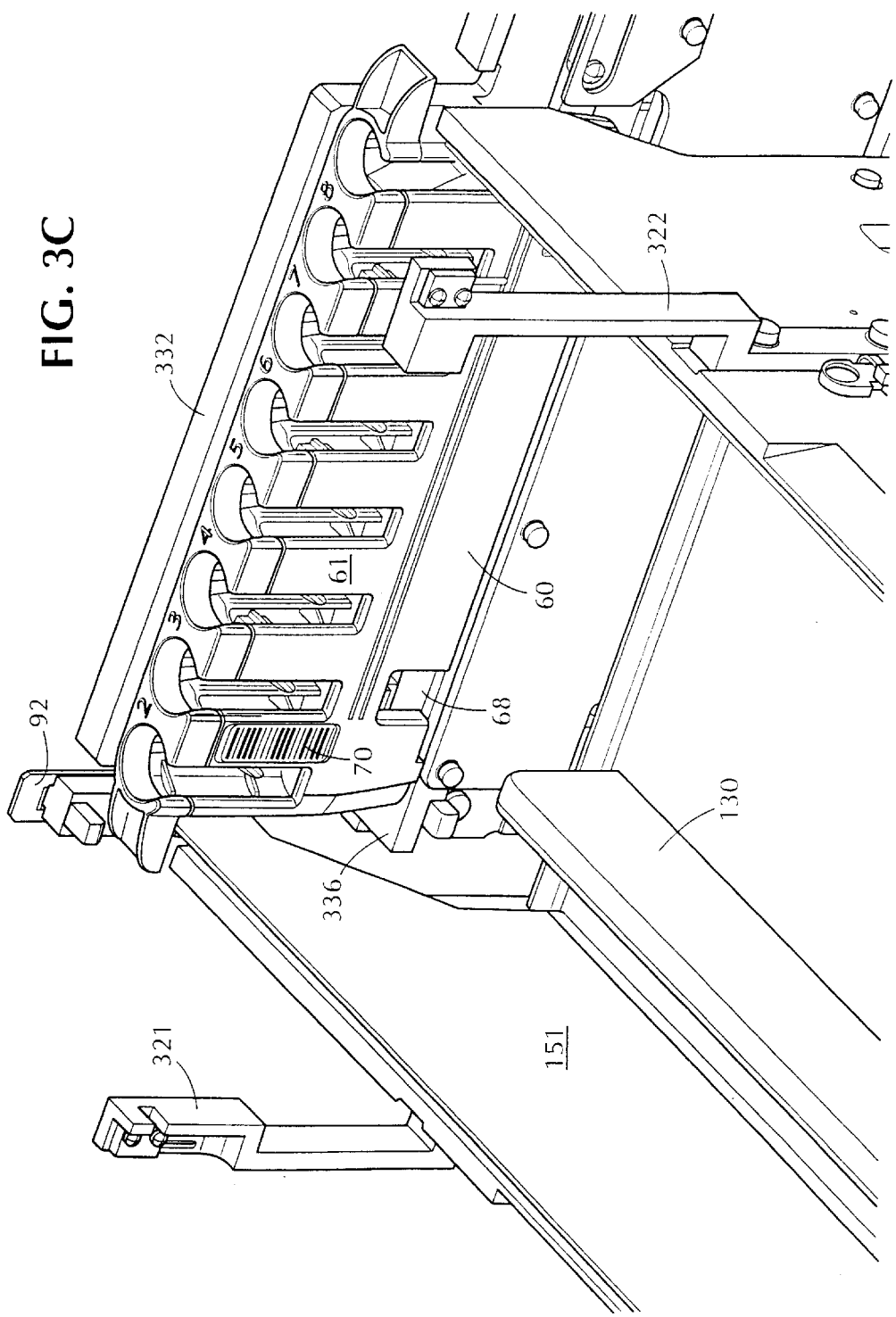

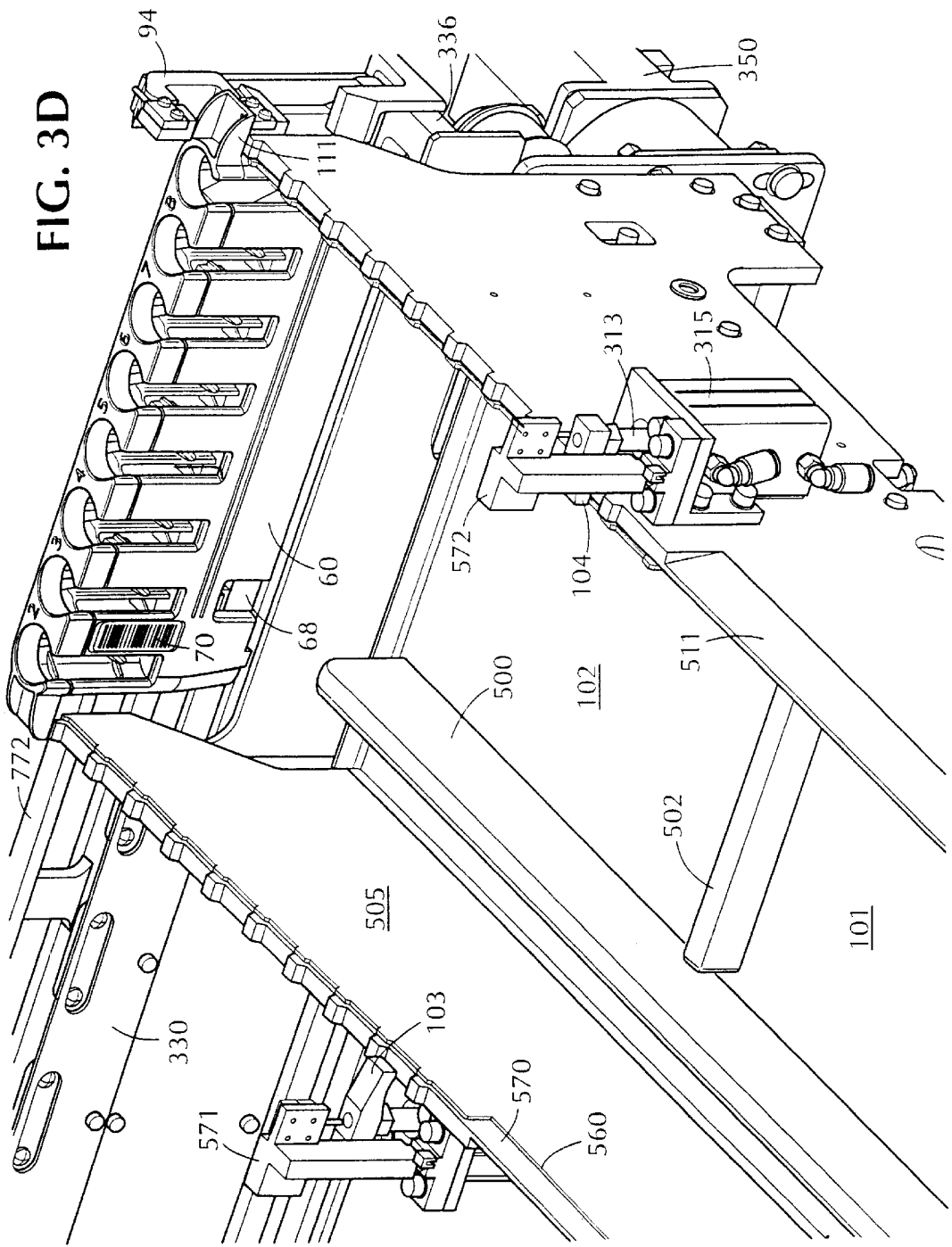

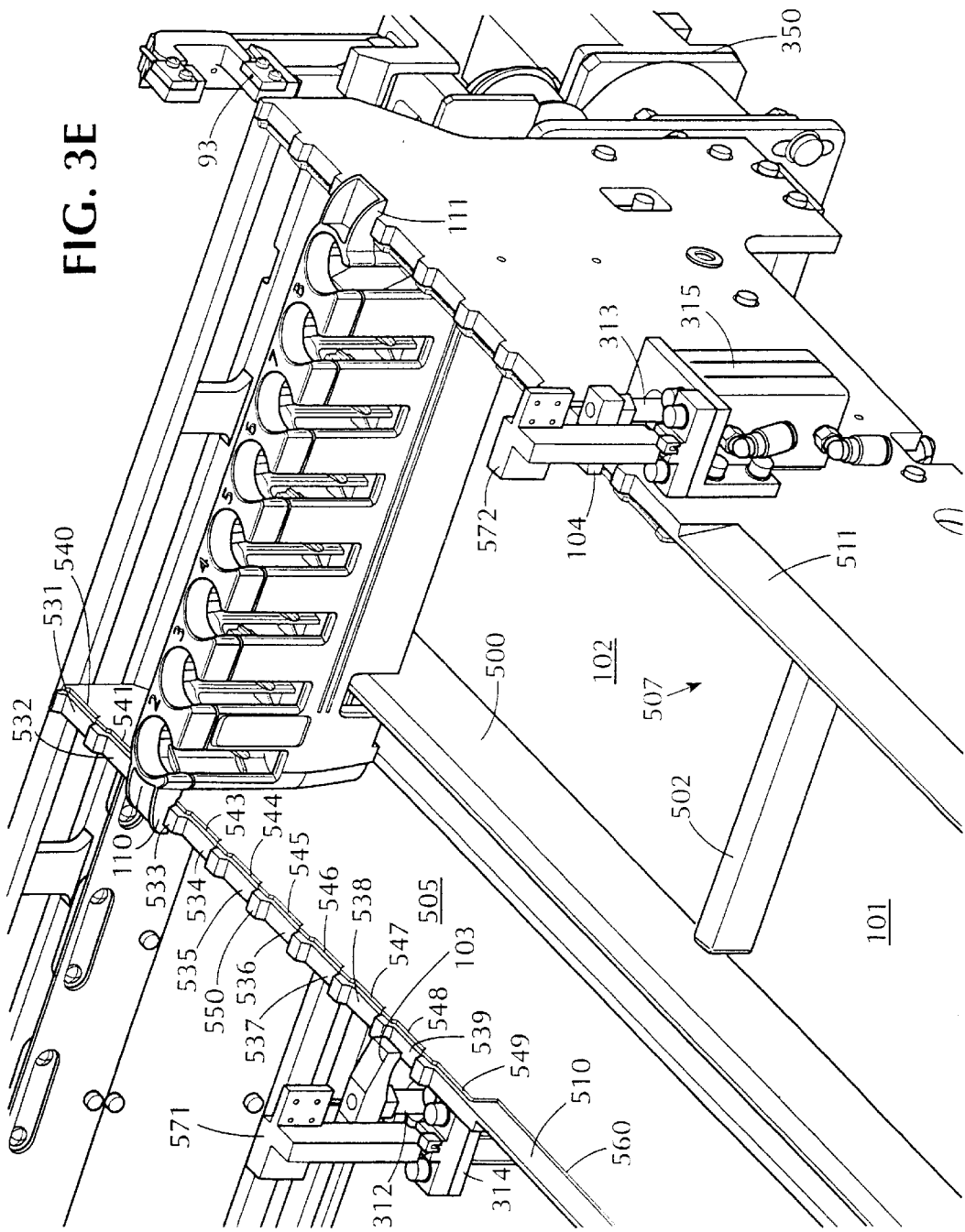

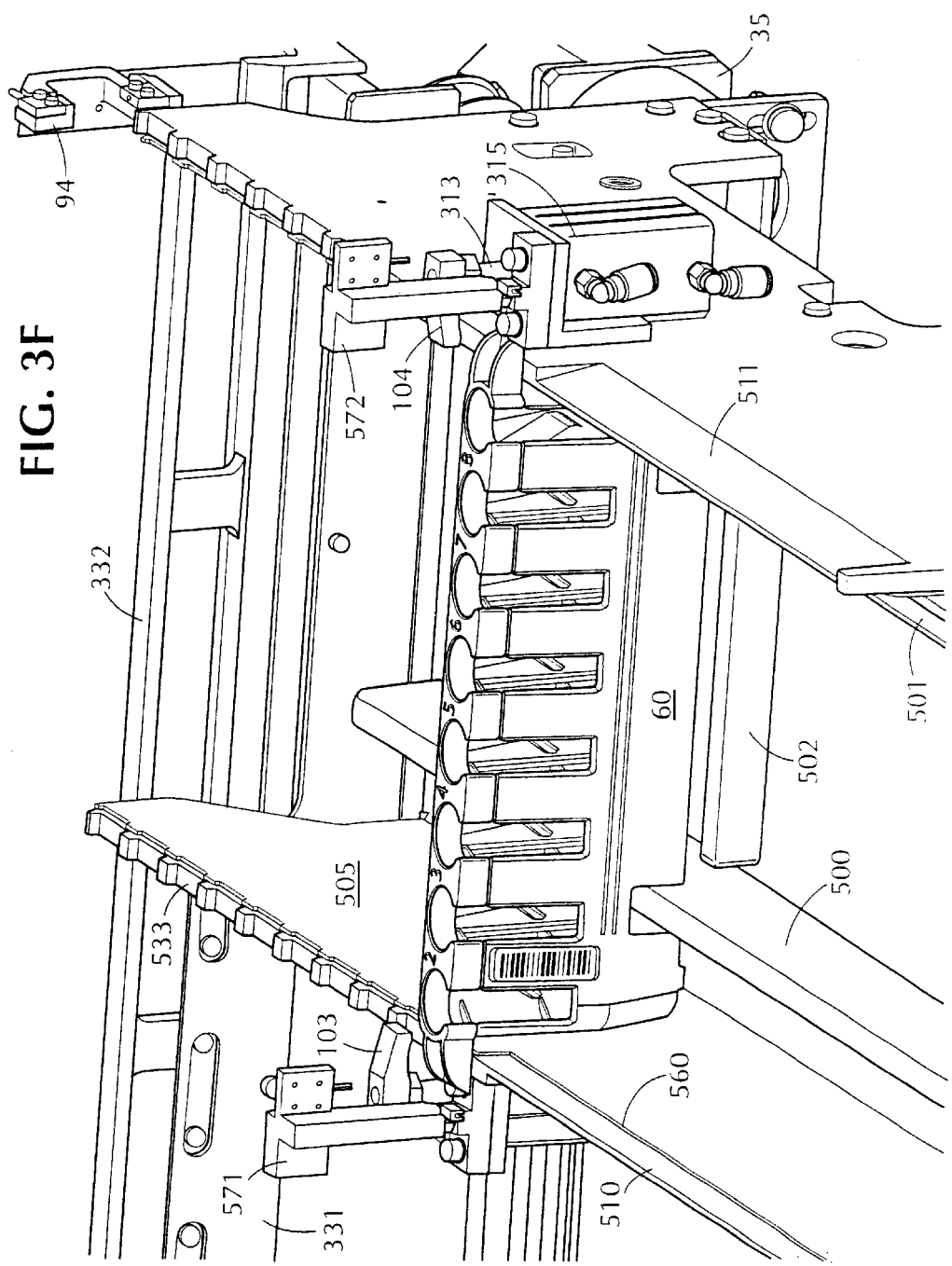

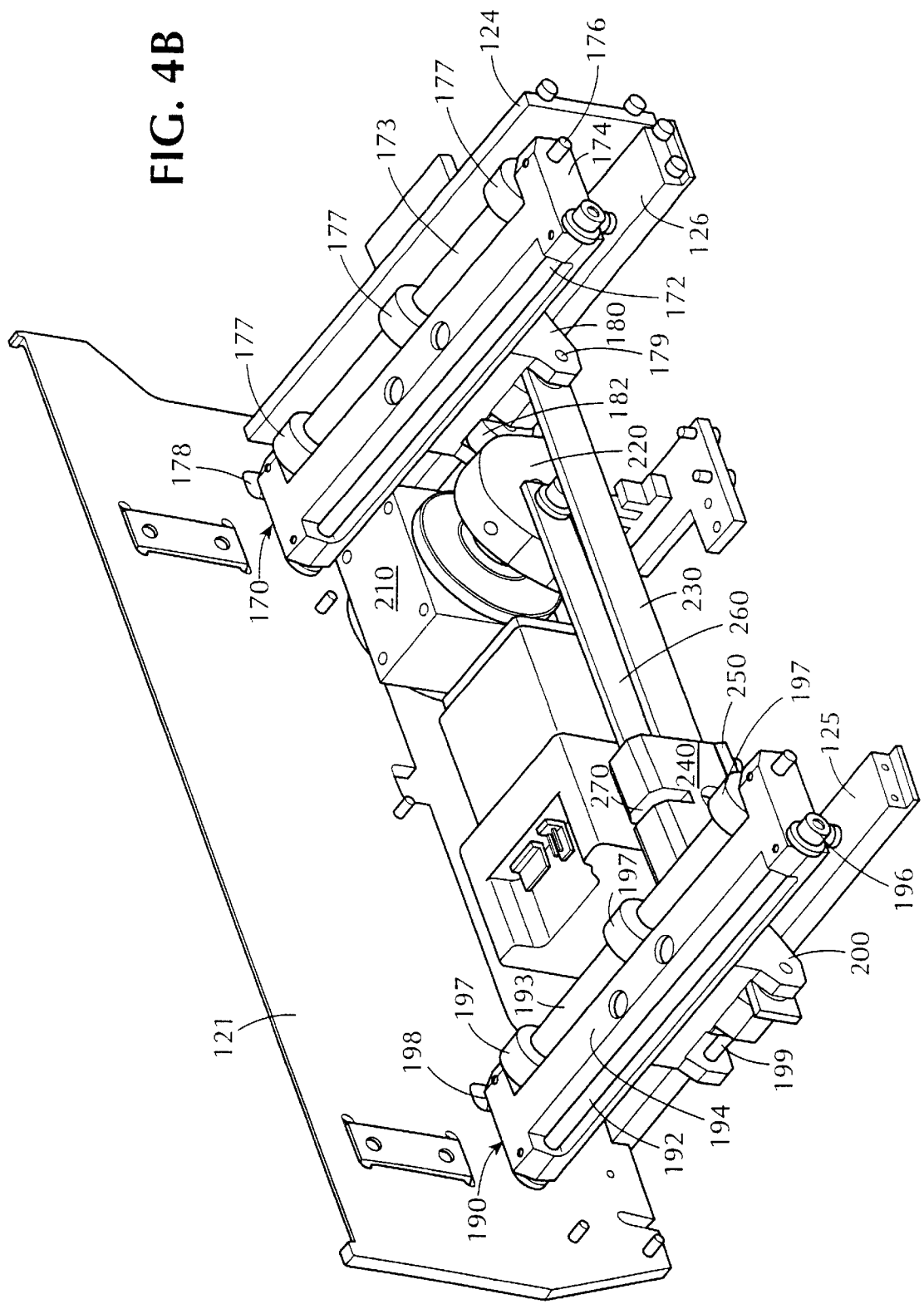

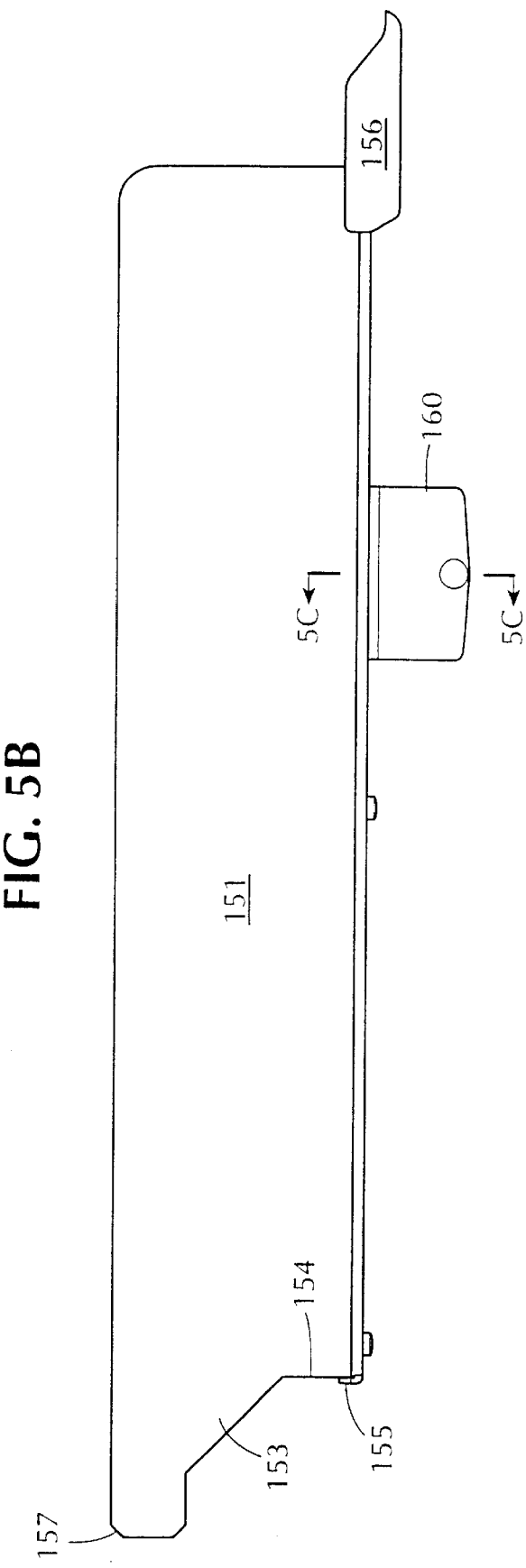

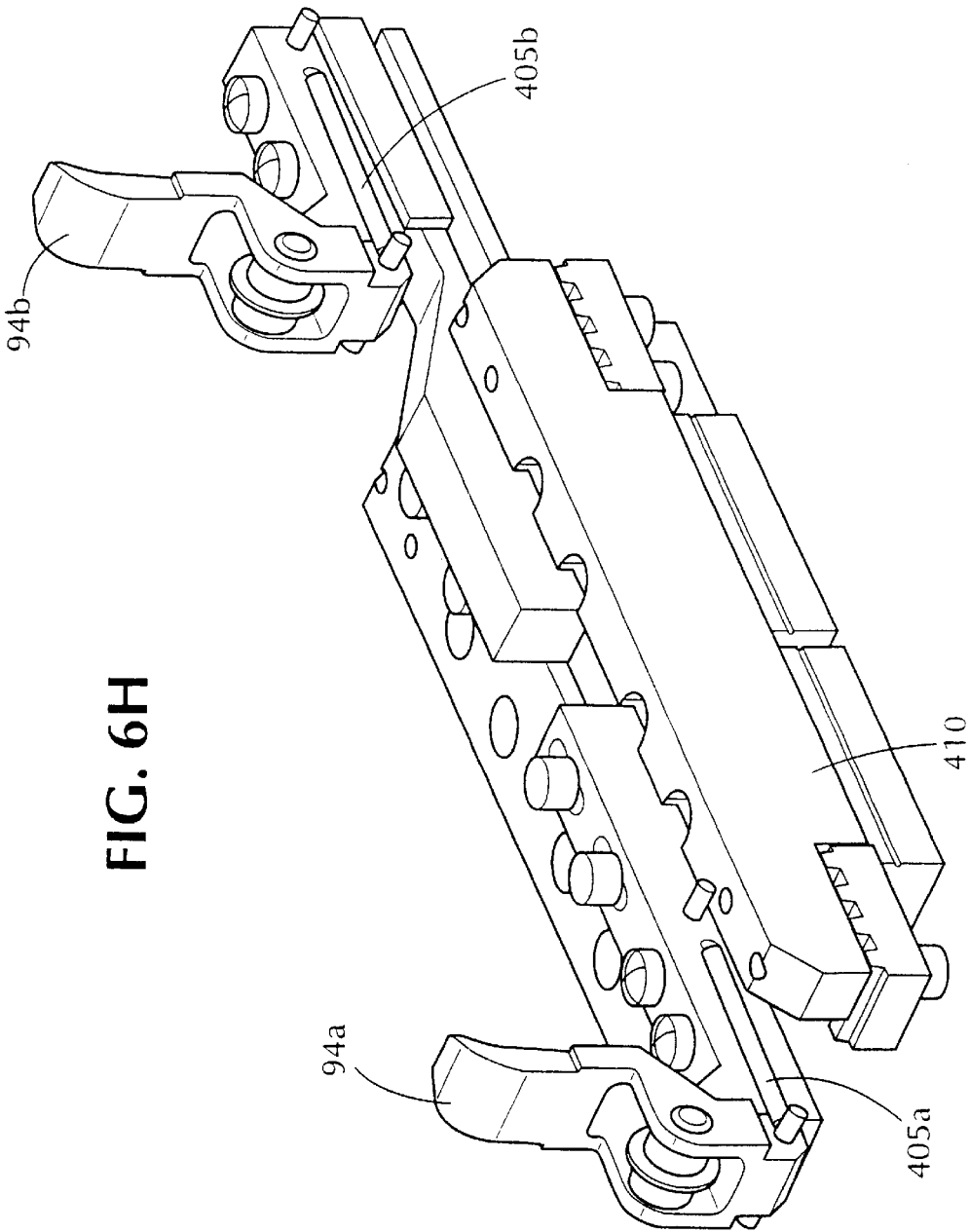

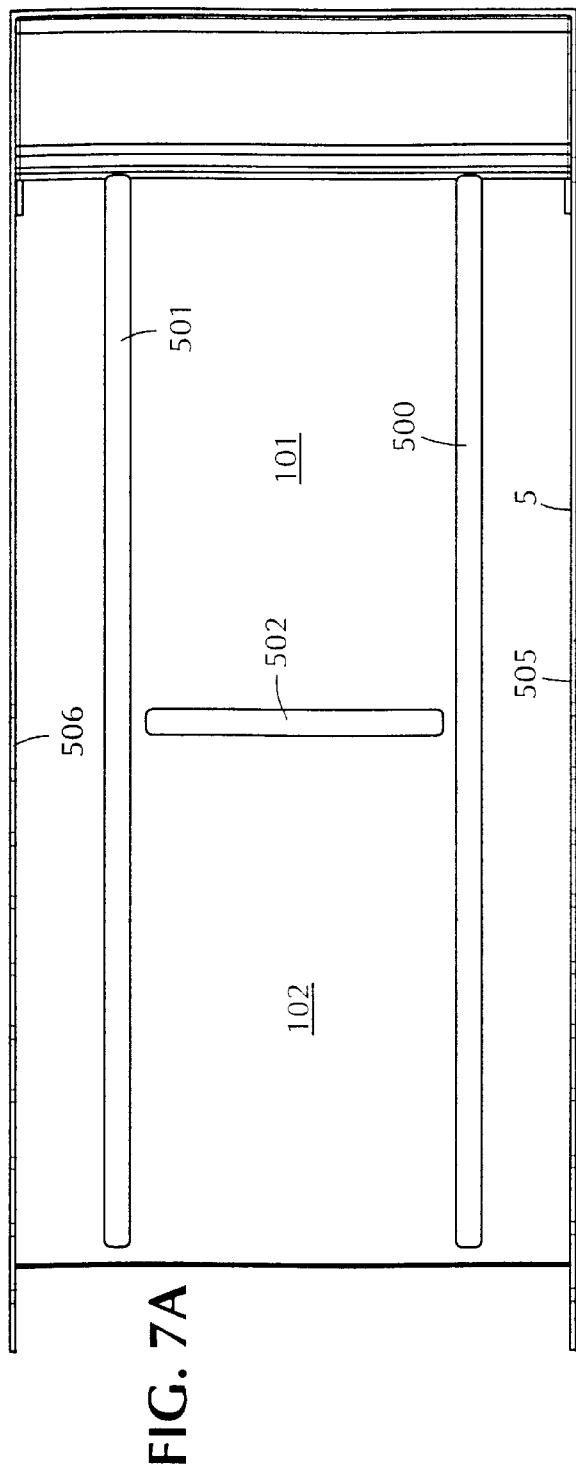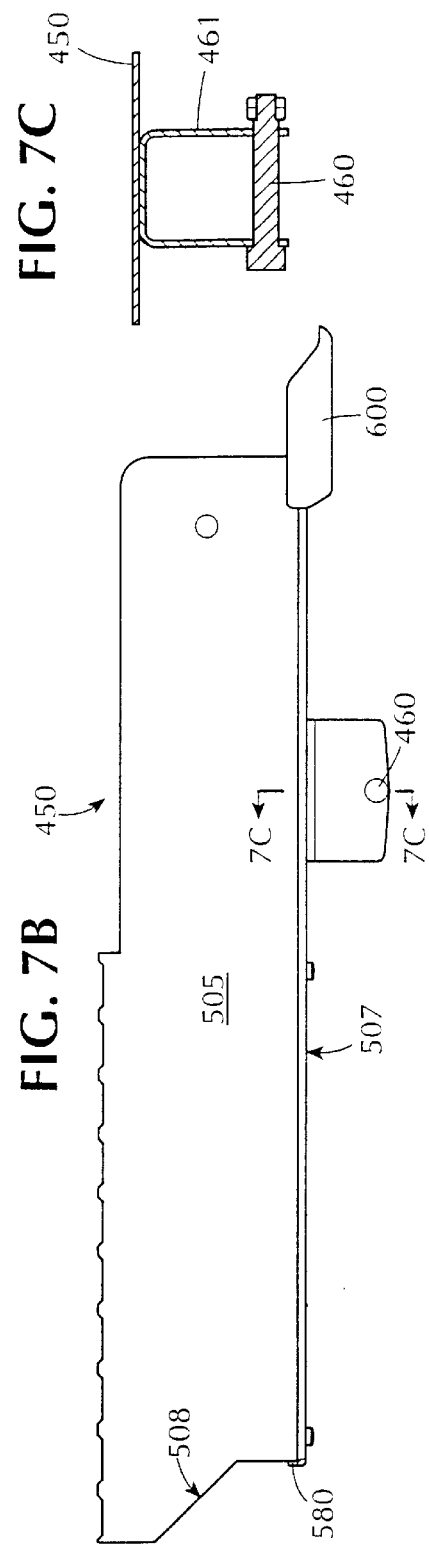

AUTOMATIC HANDLER FOR FEEDING CONTAINERS INTO AND OUT OF AN ANALYTICAL INSTRUMENT

CROSS-REFERENCE TO RELATED APPLICATIONS

This application is a divisional application of U.S. Ser. No. 09/115,391, filed Jul. 14, 1998.

This application is related to the following patent applications that are commonly assigned to Bayer Corporation and are incorporated herein by reference:

(a) United States Design Patent Applications: application Ser. No. 29/090,683 ("Gripper Finger" filed Jul. 14, 1998), now Design Pat. No. D444,157; application Ser. No. 29/090,547 ("Sample Tube Rack" filed Jul. 10, 1998), now Design Pat. No. D420,747; application Ser. No. 29/089,359 ("Sample Tube Rack" filed Jun. 15, 1998), now Design Pat. No. D421,130; and application Ser. No. 29/088,045 ("Diluent Package" filed May 14, 1998), now Design Pat. No. D411,307;

(b) United States Utility Patent Applications: application Ser. No. 09/113,643 ("Sample Tube Rack" filed Jul. 10, 1998), now U.S. Pat. No. 6.156.275; application Ser. No. 09/097,790 ("Sample Tube Rack" filed Jun. 15, 1998), now U.S. Pat. No. 6,065,617); application Ser. No. 08/985,759 ("Reagent Pack" filed Dec. 5, 1997), now U.S. Pat. No. 6,043,097; application Ser. No. 09/115,393 ("Dynamic Noninvasive Detection of Analytical Container Features Using Ultrasound" filed Jul. 14, 1998), now U.S. Pat. No. 6,227,053; application Ser. No. 09/115,080 (Robotics for Transporting Containers and Objects Within An Automated Analytical Instrument and Service Tool for Servicing Robotics" filed Jul. 14, 1998), now abandoned; application Ser. No. 09/115,777 ("Automatic Decapper" filed Jul. 14, 1998), now U.S. Pat. No. 6,257,031; application Ser. No. 09/115,640 ("Stat Shuttle Adapter and Transport Device" filed Jul. 10, 1998), now U.S. Pat. No. 6,106, 504.

FIELD OF THE INVENTION

This application relates to an automated sample handler for an analytical instrument in which racks holding capped or uncapped test tubes or other containers are input into and output from the instrument.

BACKGROUND OF THE INVENTION

Many different types of sample handlers have been used in various analytical instruments to feed multiple test tubes into and out of the instrument. Several manufacturers have utilized a sample handler system whereby the sample handler comprises an input queue, an output queue and a cross-feed. The input queue consists of an area in which racks of test tubes are input into the instrument and are transported toward the cross-feed. The racks are then transferred to the cross-feed, where one or more racks may be at a given time. The racks are indexed at set positions along the cross-feed where operations are performed on the test tubes, such as aspirating samples from the test tubes, and the racks are then moved to the end of the cross-feed adjacent the output queue where they are output to the output queue. One such system is described in U.S. Pat. No. 5,207,986. Various methods are used to transport the racks within the input queue and output queue. In some instruments, like the Chem I system sold by the Bayer Corporation, the input queue and output queue are indexed and walking beams are used to lift the base of the racks and translate them from one indexed position to an adjacent indexed position.

It is desirable to provide a sample handler that handles containers of various types, diameters and heights, whether capped or uncapped, and to permit a robotic arm to transport the containers to and from the sample handler for faster processing elsewhere without have to return the containers to a particular rack or position on the rack.

These prior art instruments do not provide this flexibility. First, they only handle a single type and style of test tube within a particular instrument. Second, these sample handlers are not designed to work in conjunction with a robot that removes containers, such as test tubes, individually from the racks for transport either within the instrument or between the instrument and a laboratory automation transport line. An entire rack would likely be lifted if a robot were to attempt to lift a test tube from a rack in the prior art instruments. Third, the input queue and output queue generally are not designed to handle uncapped test tubes because they do not stabilize the racks sufficiently and samples in open test tubes may spill. Fourth, the positions of the test tubes within a particular rack must be maintained or the instruments will be unable to track and perform the proper operations on the test tubes.

SUMMARY OF THE INVENTION

It is an object of this invention to provide an automated handler for feeding test tube racks, which may hold capped or uncapped test tubes, into an analytical instrument and output uncapped test tubes (also referred to as "open test tubes") from the instrument after the contents of the test tubes have been sampled.

It is a further object of this invention to provide an automated handler from which individual test tubes and other containers can be retrieved from racks and returned to racks individually by a robotic arm.

It is a further object of this invention to provide an automated handler for an analytical instrument that is operable in either a freestanding mode, in which racks of test tubes are manually inserted into and removed from the handler, or as a subsystem in a laboratory automation system in which test tubes are retrieved from or returned to a transport line containing test tubes.

A first aspect of the present invention is directed to a sample handler for an analytical instrument having a feeder for handling a rack, which may hold containers. The feeder comprises left and right side walls of a substantially identical height, a walking beam mechanism, and a tray, having walls of a substantially identical height, that is moved by the walking beam mechanism. When the walking beam mechanism is activated, the tray lifts a rack, which has tabs on the left and right side of the rack at a substantially identical height, from the side walls of the feeder. The feeder may be an infeed or an outfeed of a sample handler. The tray in the feeder has asymmetric guide rails to prevent the rack from skewing in the tray.

Another aspect of the present invention is directed toward an analytical instrument having a sample handler that interacts with a robotic arm on the instrument. The sample handler has an infeed, cross-feed and outfeed. A rack is input to the instrument in the infeed and is then transferred to a track on a cross-feed of the sample handler. Pusher fingers beneath the track push the rack from behind the infeed to another position, preferably behind the outfeed, where the robotic arm removes containers for transport elsewhere in the instrument. An ultrasonic range sensor detects whether a rack has been inserted into the infeed and whether the rack is skewed when it is placed on the cross-feed track behind the infeed. A reader of machine-readable code, such as a bar code reader, and an ultrasonic liquid level sensor are positioned adjacent the track to identify the container and profile the containers before the robotic arm removes the containers from the rack.

Another aspect of the present invention is directed to a sample handler having an outfeed with a walking beam mechanism to move the racks with a movable tray. A rear area of the tray has side walls that have a plurality of detents separated by ridges to capture a rack within the detents and hold the rack in a fixed position for the return of containers to the racks.

Another aspect of the present invention is directed toward a sample handler having an infeed, cross-feed, outfeed, and stat shuttle. The stat shuttle provides for the inputting of containers on a priority basis, including containers that may otherwise be input on a rack placed in the infeed. The stat shuttle also permits the inputting and outputting of a variety of containers. Like the cross-feed, the stat shuttle has a bar code reader and ultrasonic liquid level sensor to identify and profile containers in the stat shuttle. Thus, containers that are unidentified or not properly profiled in the cross-feed may be transferred to the stat shuttle for another attempt at identification and profiling.

BRIEF DESCRIPTION OF THE DRAWINGS

The inventions and modifications thereof will become better evident from the detailed description below in conjunction with the following figures in which like reference characters refer to like elements in which:

FIG. 1A is a perspective view of the sample handler of the present invention for an analytical instrument and some adjacent components of the instrument with several panels and doors of the instrument situated above the sample handler;

FIG. 3C is a perspective view of portions of the infeed and cross-feed with the test tube rack positioned in the infeed end of the cross-feed;

FIG. 3D is a perspective view of portions of the outfeed and cross-feed with the test tube rack positioned in the outfeed end of the cross-feed;

FIG. 3E is a perspective view of portions of the outfeed and cross-feed with the test tube rack positioned in the rear area of the outfeed which is inaccessible to an operator;

FIG. 3F is a perspective view of portions of the outfeed and cross-feed with the test tube rack positioned in the forward-most position in the rear area of the outfeed with tabs on the rack positioned under clamps that are in their open position;

FIG. 4B is a perspective view of the walking beam mechanism and several cross-beams of the infeed attached to only the right wall of infeed, the walking beam mechanism of the outfeed being similar;

Figure 6A:
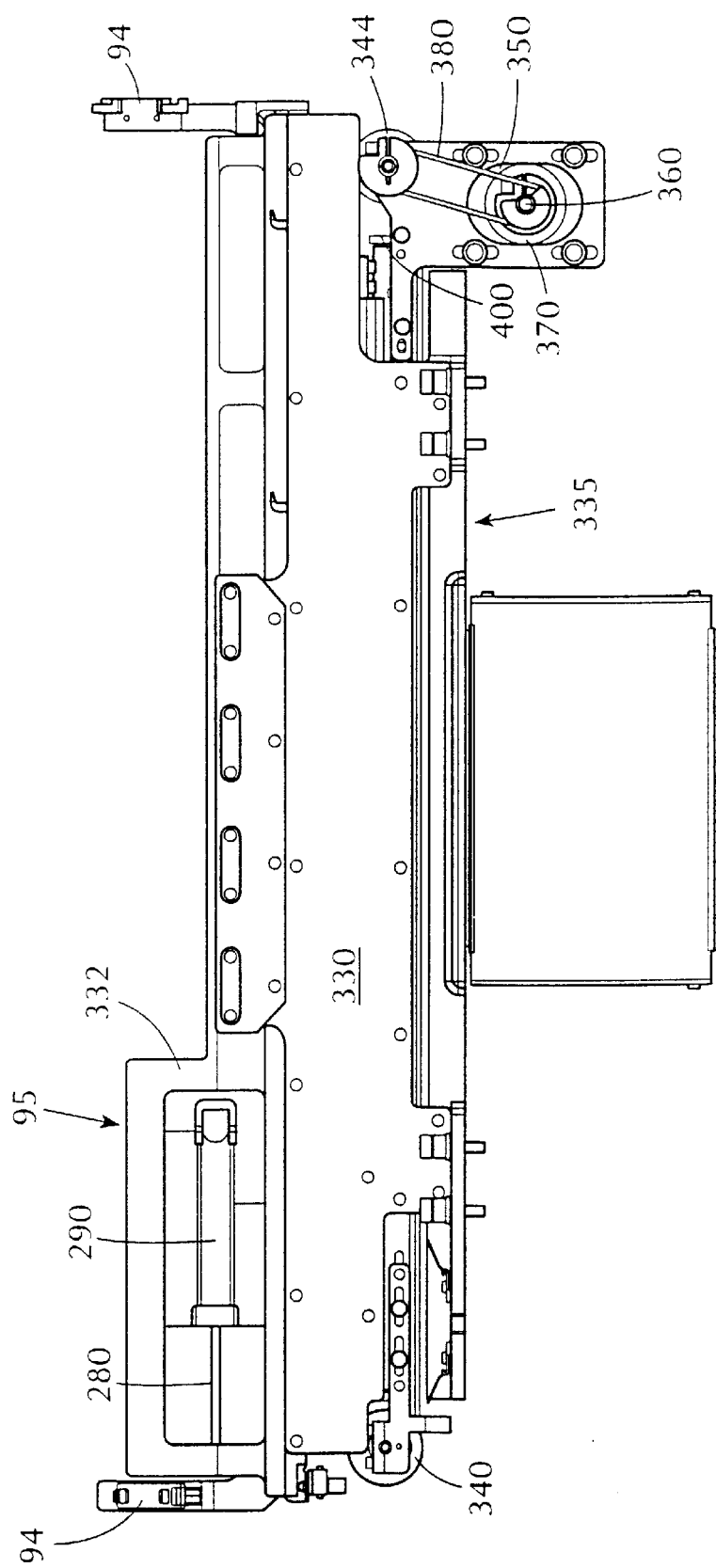
Figure 6B:
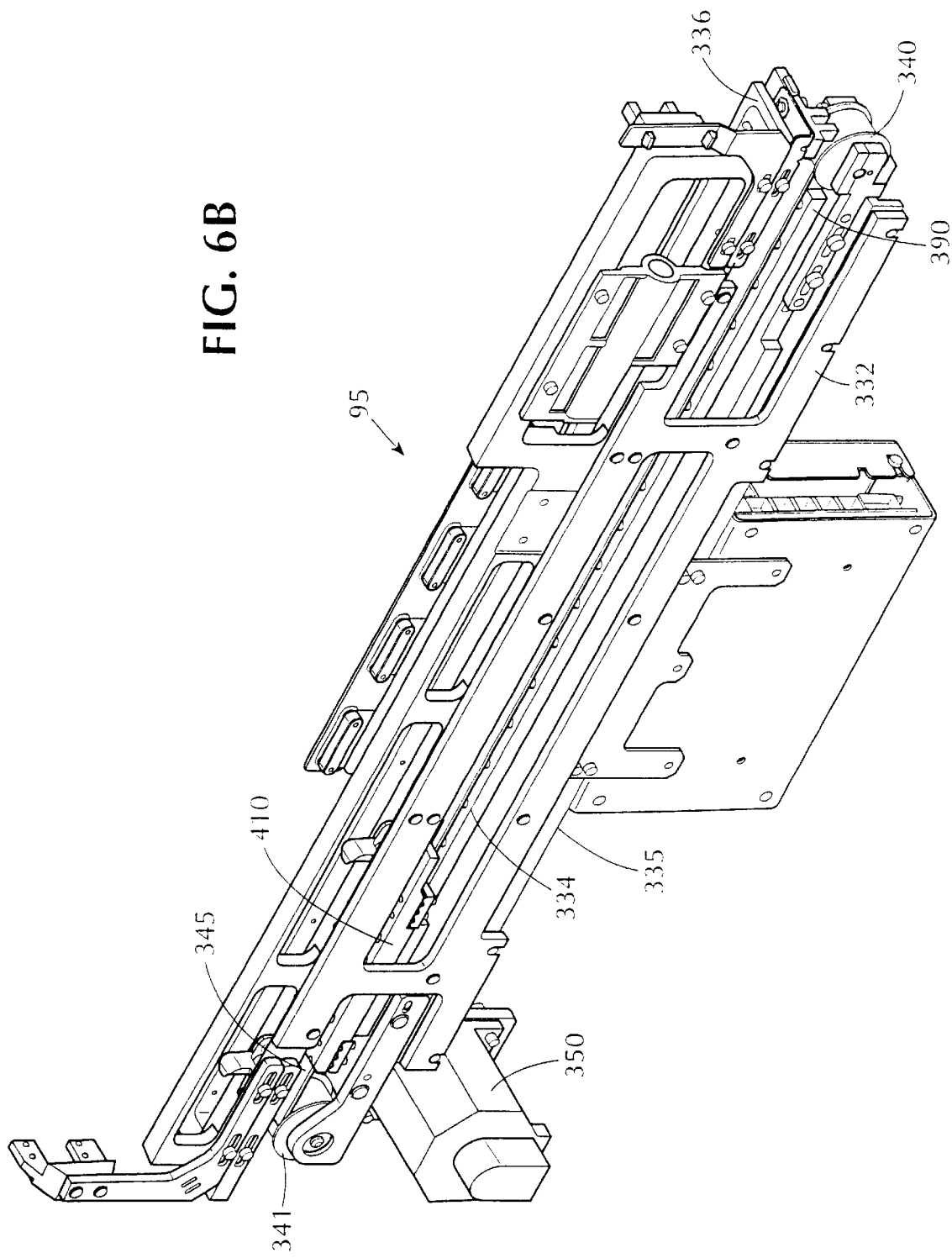
Figure 6C:
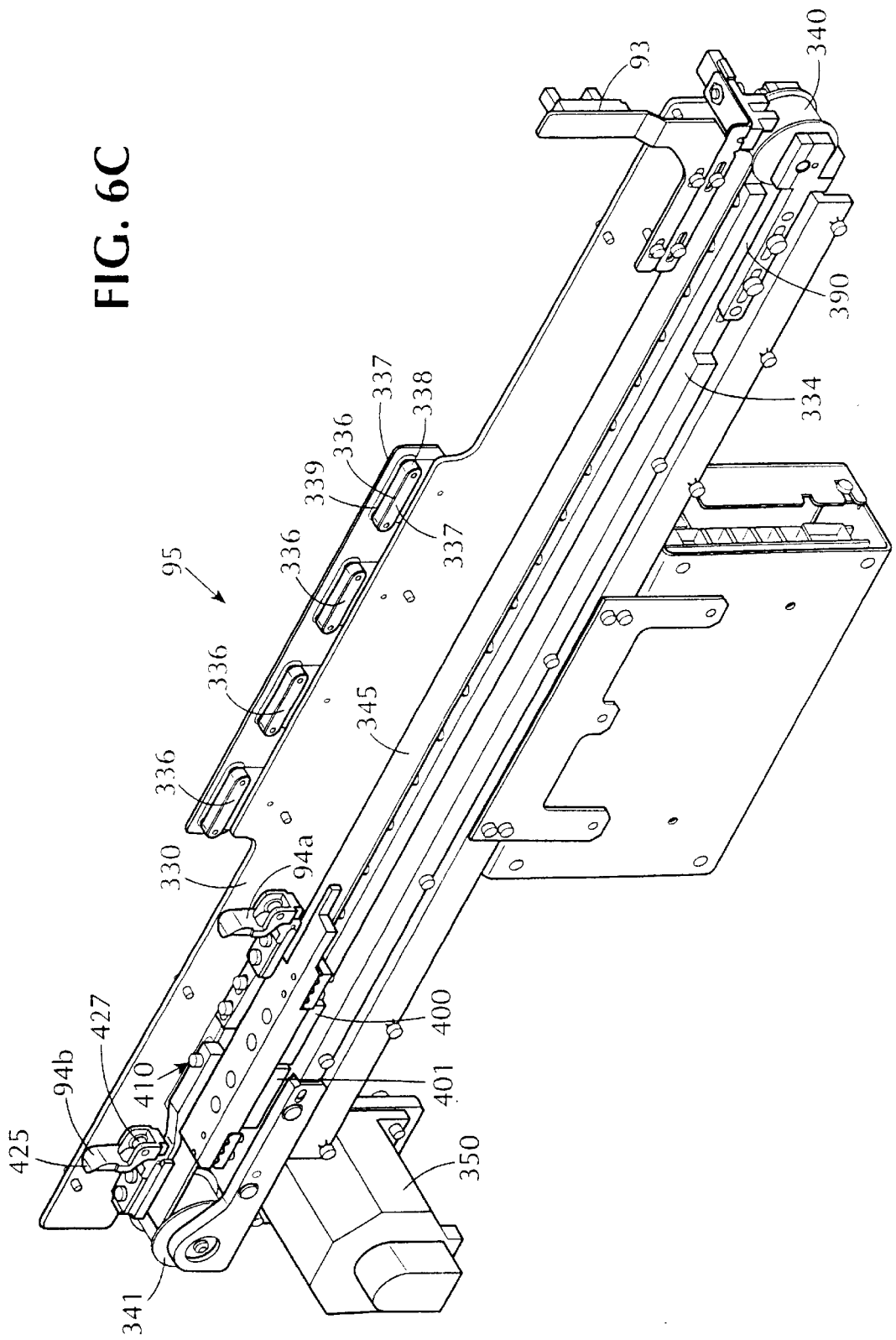
Figure 6D:
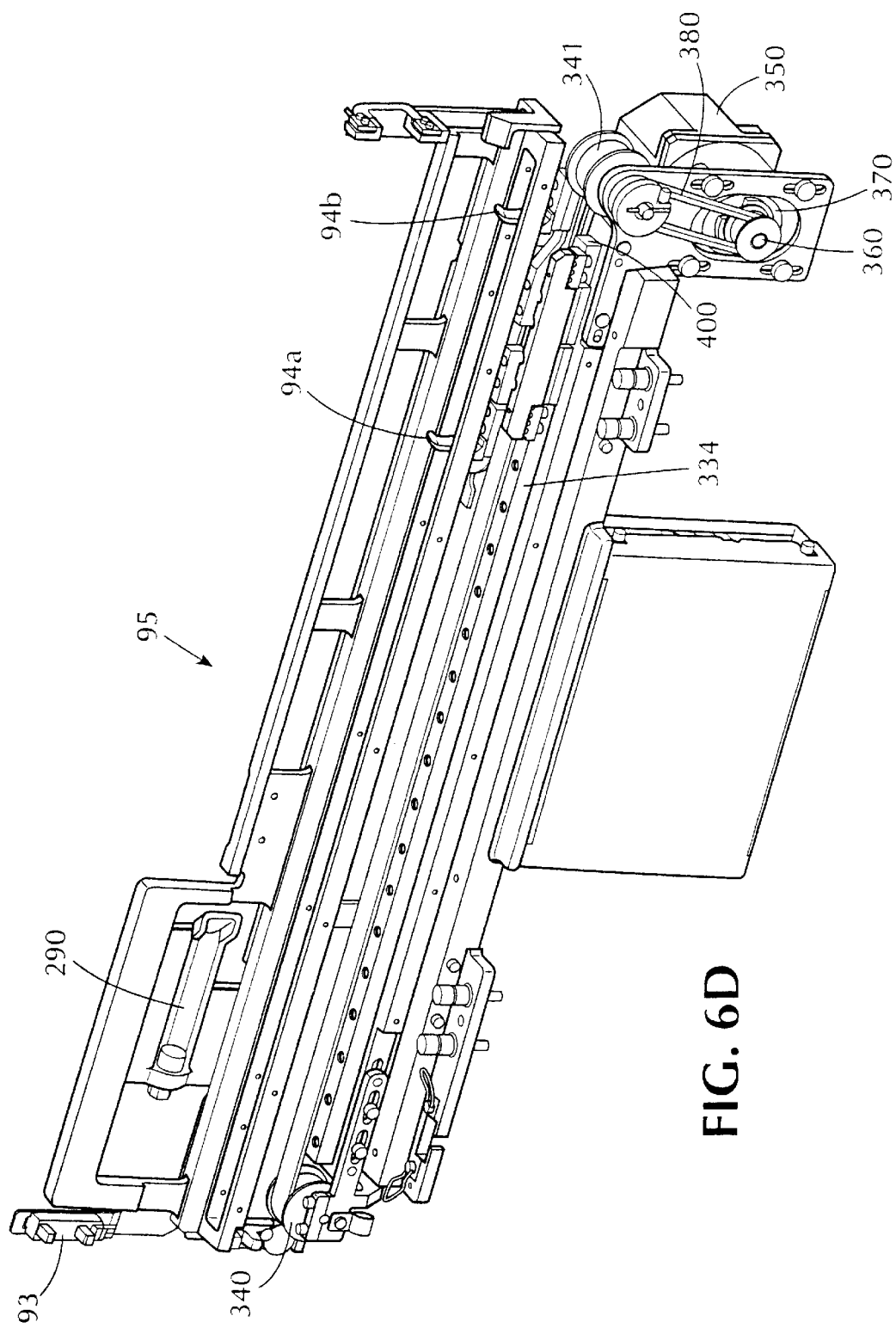
Figure 6E:
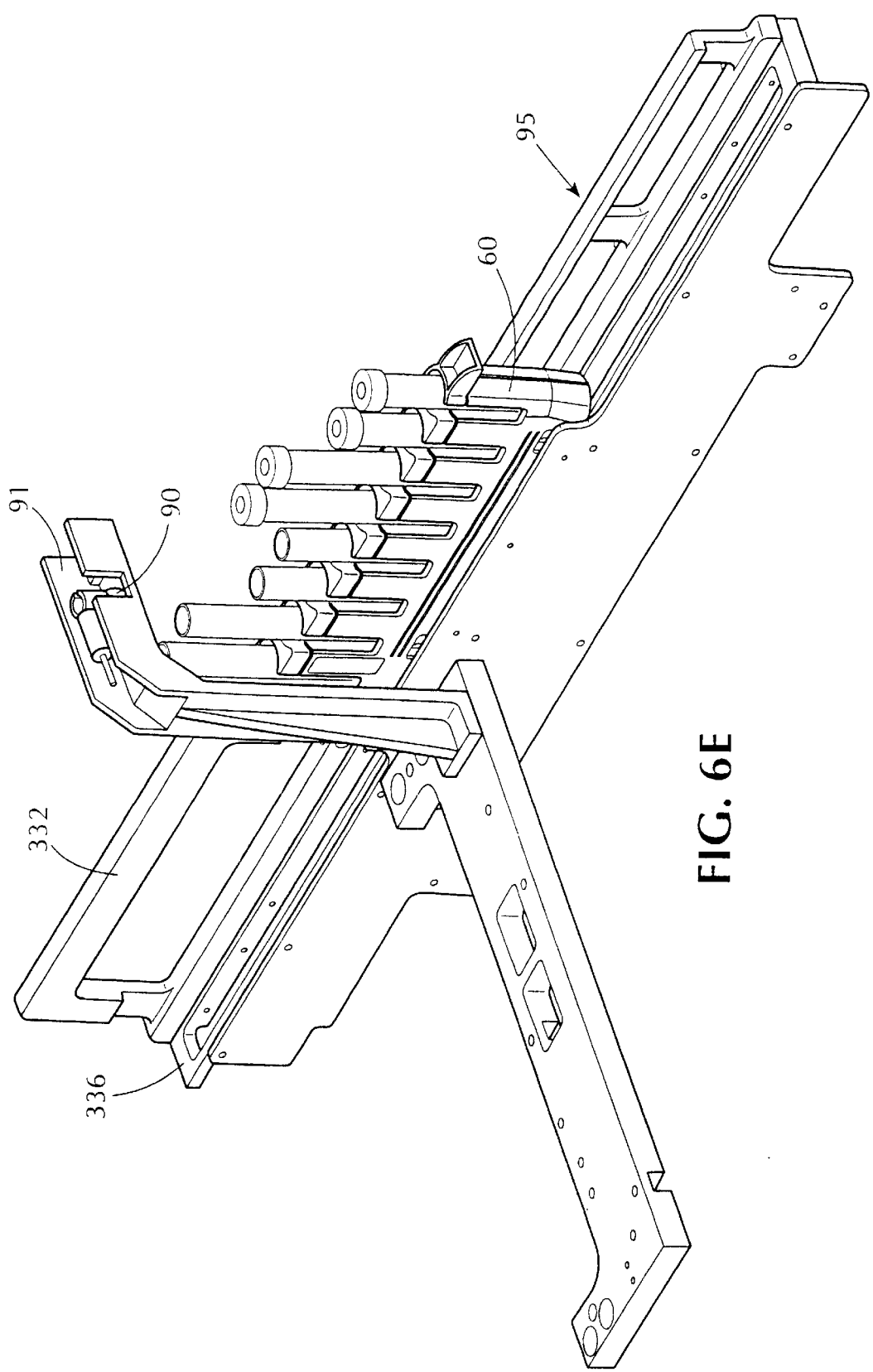
Figure 6F:
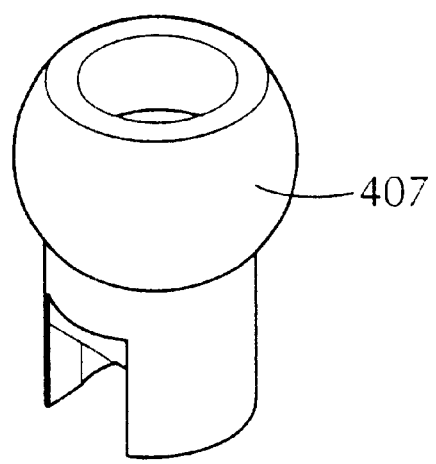
Figure 6G:
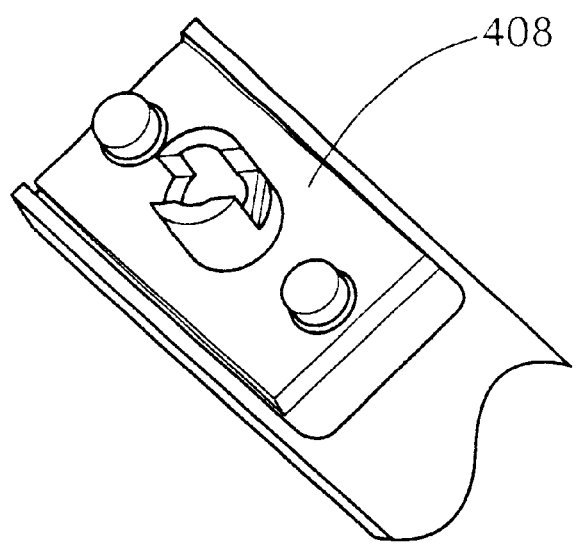
Figure 8A:
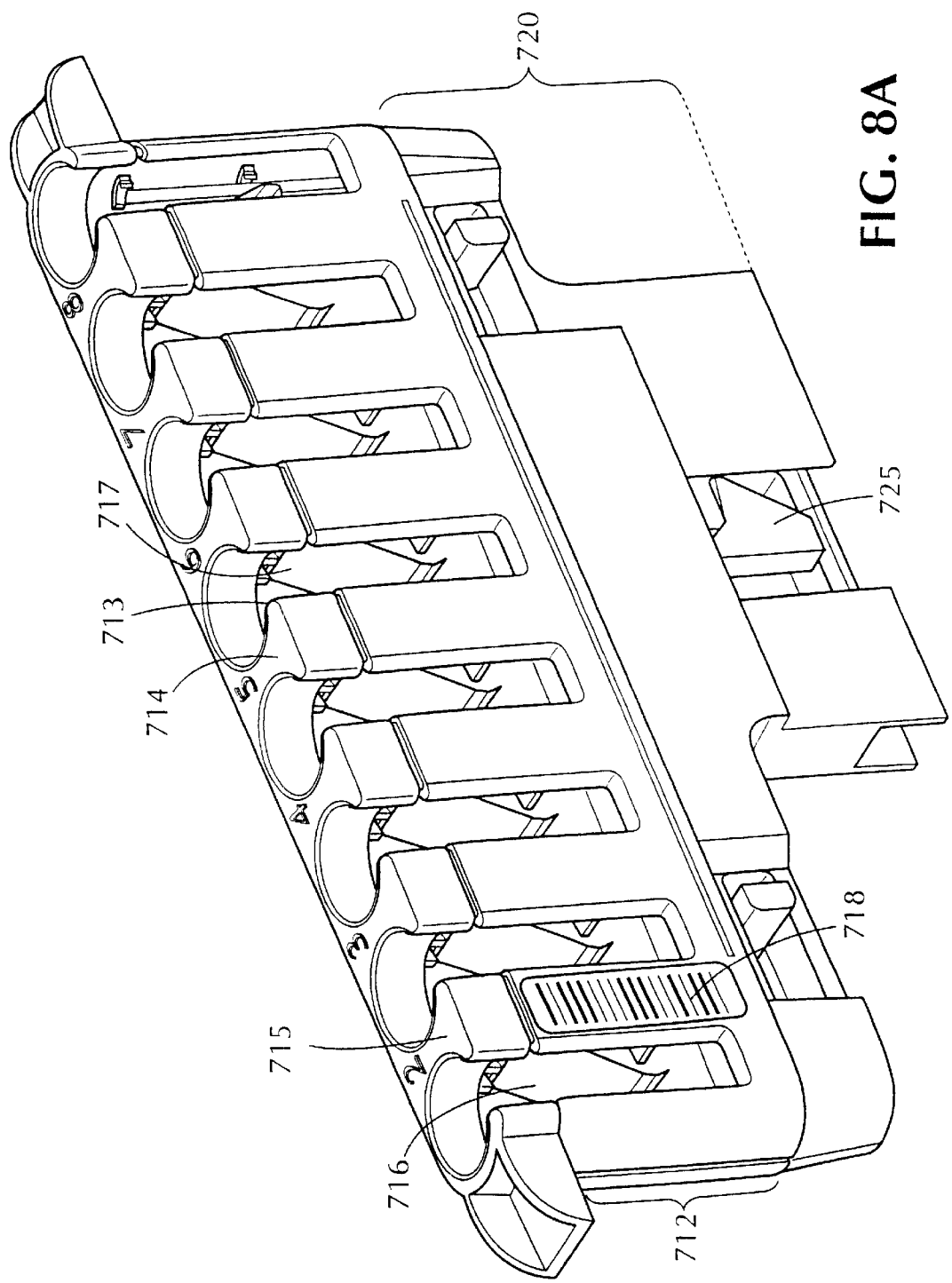
Figure 8B:
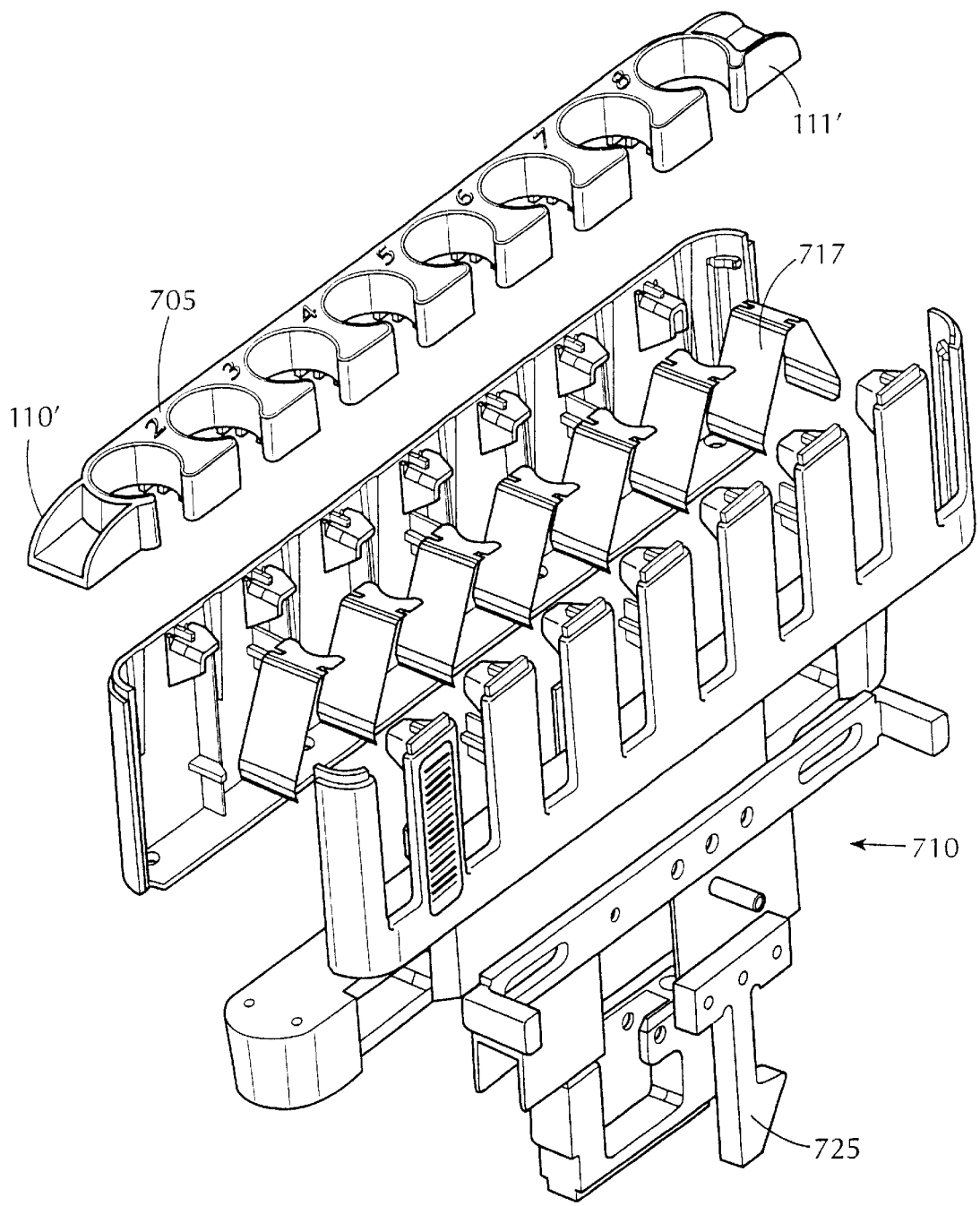
Figure 9:
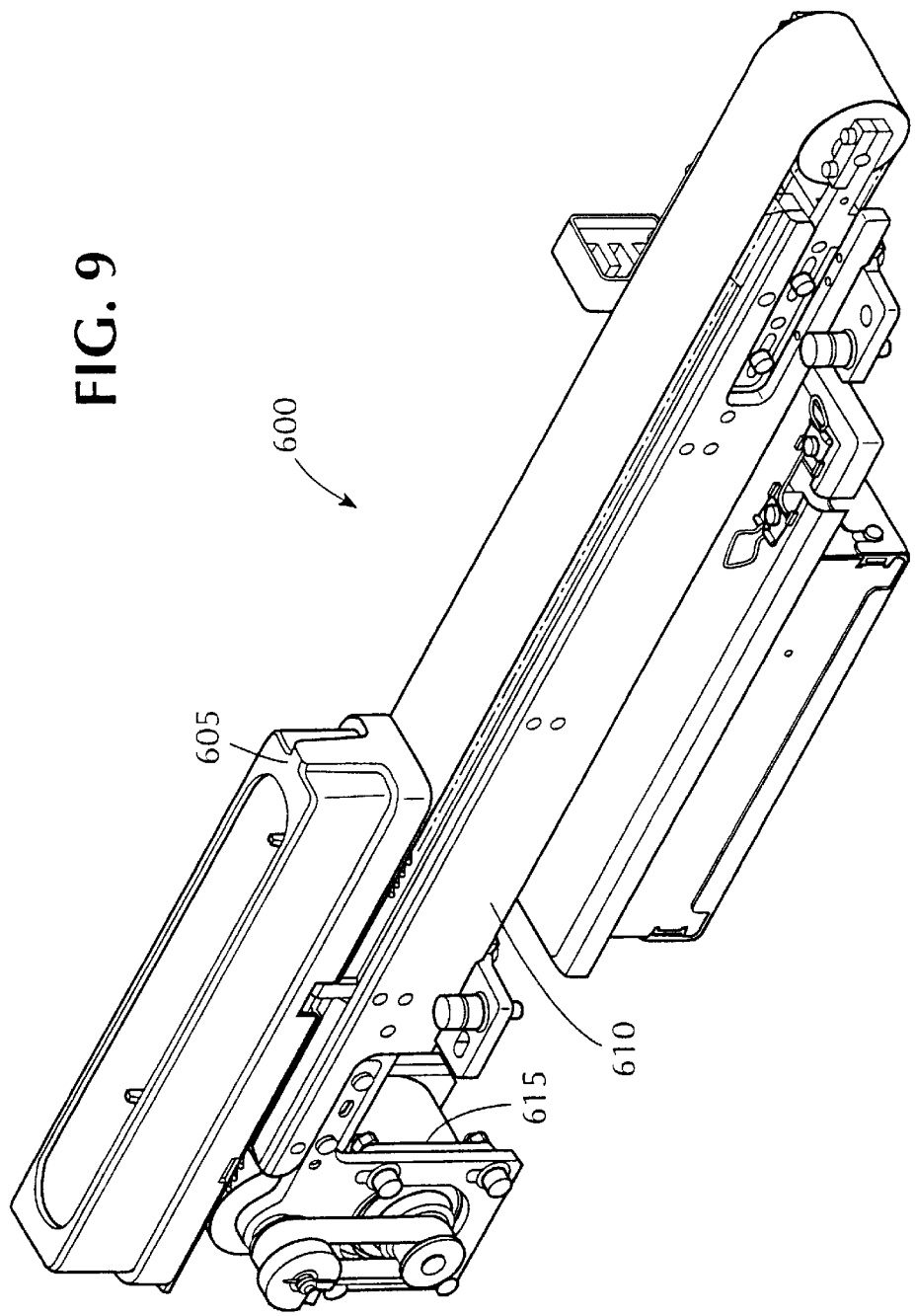
Figure 10A:
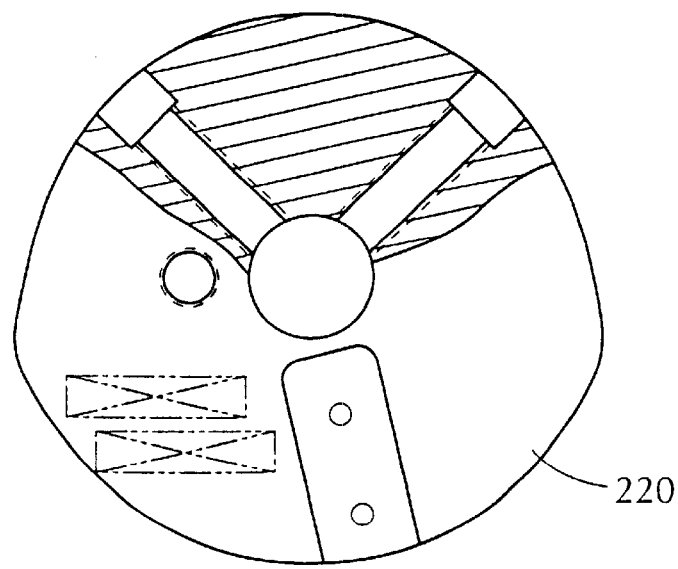
Figure 10B:
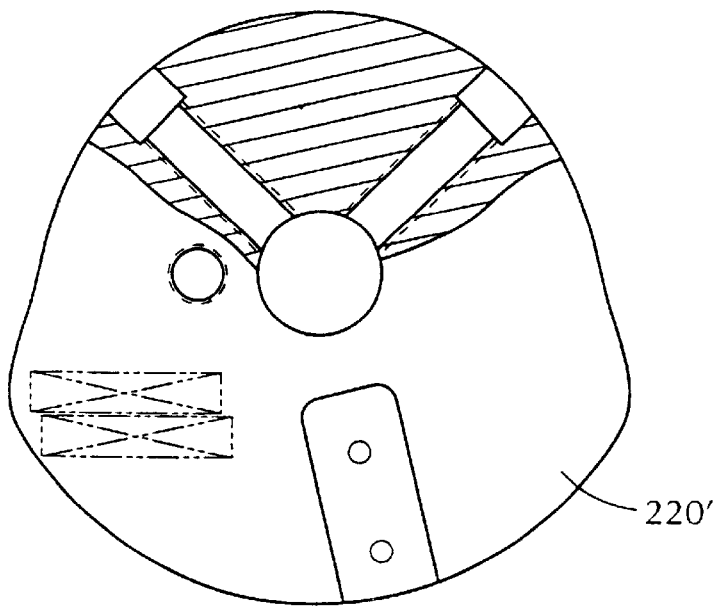

FIG. SC is a cross-sectional view of a portion of the infeed tray along line C—C of FIG. 5B;

FIG. 6A is front view of the cross-feed;

FIG. 6B is a perspective view of the cross-feed from the rear of the cross-feed, FIG. 6C is a perspective view of the cross-feed of FIG. 6B from the rear of the cross-feed with the main floor, rear wall, rack endstop, mount bracket and track removed;

FIG. 6D is a perspective view of the cross-feed of FIG. 6C with the front wall removed;

FIG. 6E is a front perspective view of the cross-feed with the ultrasonic liquid level sensor positioned above a rack with containers;

FIG. 6F is a perspective view of the gimbal in which the ultrasonic liquid level sensor is mounted;

FIG. 6G is a perspective view of the sensor holder to which the gimbal is mounted;

FIG. 6H is a perspective view of the platform;

FIG. 7A is a top view of the outfeed tray;

FIG. 7B is a side view of the outfeed tray;

FIG. 7C is a cross-sectional view of a portion of the outfeed tray along line C—C of FIG. 7B FIG. 8A is a front isometric view of the laboratory automation adapter;

FIG. 8B is an exploded view of the laboratory automation adapter of FIG. 8A;

FIG. 9 is an isometric view of a stat shuttle that may included in the sample handler;

FIG. 10A is a side elevational view of the cam profile for the infeed walking beam mechanism; and FIG. 10B is a side elevational view of the cam profile for the outfeed walking beam mechanism.

DETAILED DESCRIPTION OF THE PREFERRED EMBODIMENT

Referring to FIGS. 1A–1C 2A and 2B an analytical instrument 10 has a sample handler 20 according to the present invention to input and output containers to instrument 10. Sample handler 20 comprises an infeed (or "input queue") 80, a cross-feed 95, and an outfeed 100 (or "output queue"). Infeed 80 and outfeed 100 are positioned parallel to one another along their length. Cross-feed 95 is positioned behind infeed 80 and outfeed 100 and extends at least from behind the leftmost wall of infeed 80 to behind the rightmost wall of outfeed 100.

Instrument 10 has one or more modules (not shown) in addition to sample handler 20 to perform various operations, including analyses, on the contents of a test tube. Various panels 30, 40, including doors 35, 45 and a tower 50 for electronic controls are positioned above sample handler 20 and prevent access by an operator to the rear of sample handler 20, including a rear area 82 of infeed 80 and the rear area 102 of outfeed 100 as well as the entire cross-feed 95 during operation of the sample handler. If doors 35 or 40 are opened, sample handler 20 (and one or more robotic arms that may interact with the sample handler) stops. The operator may access a front area 81 of infeed 80 and a front area 101 of outfeed 100, however, while instrument 10 is operating.

Multiple microcontrollers control the operation of instrument 10 and communicate with one another over a CAN bus. One of these controllers is a sample handler controller, which may comprise a control board based on the Intel 386EX microprocessor. Sample handler controller communicates with and serves as a master controller for a separate controller for cross-feed 95 as well as separate controllers for the robotics which operate in conjunction with sample handler 20. Cross-feed 95 may be a CAN node and the cross-feed controller may comprise a Phillips 8051 microprocessor to control the high current stepper motor of cross-feed 95. Software in the sample handler controller provides a user interface to permit the user to control various aspects of sample handler 20.

Preferably, in order to save on processing time by the controllers, a grid of all of the potential "registration locations" from and to which a container may be moved is mapped out in workstation software before instrument 10 is first activated. In the disclosed embodiment, these registration locations include eight locations in the outfeed side of cross-feed 95, one location per tube receptacle 66 on one of racks 60, and 72 locations in rear area 102 of outfeed 100, including 8 possible tube receptacle locations on each of 9 possible racks in rear area 102.

A control keypad is incorporated into tower 50 on the front of sample handler to permit the operator to stop the motion of infeed 80, cross-feed 90, or outfeed 100 in the event of a jam or to clean a spill.

Test Tube Racks

Test tubes or inserts, such as Microtainers®, or tubes with Ezee-Nest® inserts (generically referred to below as "test tubes") are placed into test tube racks 60 (FIG. 2B) designed specifically for transporting the test tubes through sample handler 20. A bar code label 70, or some other form of machine-readable identification code, is affixed to each of racks 60 and, similarly, a bar code label 71, or some other form of machine-readable identification code, is affixed to each test tube to allow instrument 10 to identify the racks 60 and test tubes and are used to identify, through a work order generally entered by the operator at the workstation or downloaded from a hospital laboratory system, what must be done with the test tubes. Custom-designed racks 60 are the subject of the referenced patent application assigned Ser. No. 09/097,790, now U.S. Pat. No. 6,065,617.

Each of racks 60 may hold as many as eight test tubes, which may be test tubes of various types, heights, and diameters, in individual tube receptacles 66 separated by side walls 64. A lateral front wall 61 of each rack has openings 63 in front of each test tube location that are sufficiently large to expose the bar code label 71 on each test tube to be read by a bar code reader 55 (FIG. 1B) (or, if a machine readable identification code other than bar codes are used, a device suitable for reading that code) while a lateral rear wall 65 of each rack is closed. Test tubes are placed in the rack 60 by the operator and held in place with a spring, preferably a vertical leaf spring 67, in each tube receptacle 66. The test tubes must be firmly seated in the tube receptacles 66 to hold the test tubes securely, to prevent collisions of an improperly seated test tube with various obstructions (such as panel 30), and to provide precise positioning of the test tubes to permit bar code reader 55 to identify each test tube and an ultrasonic liquid level sensor 90 to determine the level of liquid therein and to detect the presence of caps on test tubes.

Figure 3A:
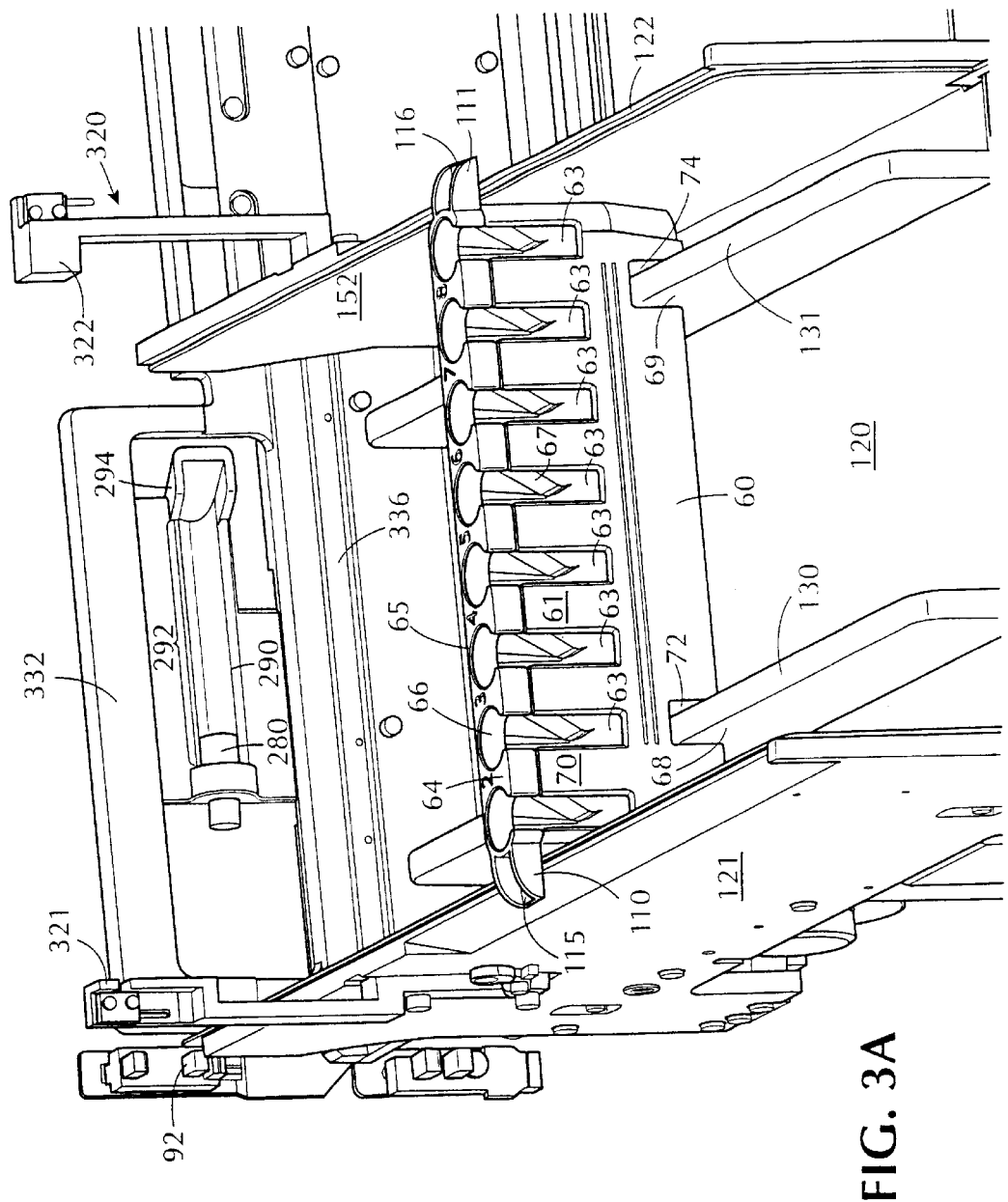
FIG. 3A is a perspective view of portions of the infeed and cross-feed of the sample handler with a test tube rack in a front operator-accessible area.

Tabs 110, 111 (or "ears") on each side of racks 60 are located at the same height on each side of racks 60 and are used to hold racks 60 upright and to lift and advance the position of rack 60 in infeed 80 and outfeed 100 as explained below. Tabs 110, 111 are also used by sensors 92, 93 (FIGS. 3A and 3E) in cross-feed 95 to detect the presence of a rack 60 at either side of cross-feed 95 and to provide a reference level for profiling by ultrasonic liquid level sensor 90. Recesses 115, 116 on each of respective tabs 110, 111 are provided to allow a pair of clamps 103, 104 in outfeed 100 to hold rack 60 in place.

Two openings 68, 69 are provided at the bottom of racks 60 (FIG. 2A) for racks 60 to travel over guide rails 130, 131 on infeed tray 120 as further described below. Openings 68, 69 in the bottom of racks 60 have a width W sufficient to fit pusher fingers 94a, 94b within openings 68, 69 with the pusher fingers in the raised position without contacting the rack and to prevent the rack from camming on guide rails 130, 131 on tray 120 and guide rails 500, 501 on outfeed 100 (as indicated by pusher fingers shown as dotted lines in FIG. 2B). On the right side of each opening is a respective window 72, 74 to be engaged by respective pusher fingers 94a, 94b (FIG. 6C) on cross-feed 95. On the left side of and continuous with openings 68, 69 are internal voids 76, 78 that provide the additional clearance necessary for fingers 94a, 94b to first disengage from windows 72, 74 before being pivoted downward to the right as the platform 410 to which they are attached moves to the left of cross-feed track 336 (described below) when pusher fingers 94a, 94b hit respective walls 79a, 79b on racks 60. Openings 68, 69 are positioned asymmetrically along the length of the rack 60 (as are guide rails 130, 131 in infeed tray 120) to intuitively guide the operator to insert racks 60 into infeed 80 in only one direction with the front wall 61 of racks 60, the bar code labels 70, 71 on racks 60 and test tubes, respectively, facing the front of infeed 80 to be read by bar code reader 55 on cross-feed 95.

A ballast (not shown) weighing approximately 35–40 grams is incorporated within each of racks 60 during assembly and is located between windows 72, 74 to stabilize racks 60.

The movement of racks 60 within sample handler 20 will be described in detail below.

Infeed

An operator inserts test tubes into racks 60 and inserts racks 60 into infeed 80. Infeed 80 holds multiple racks, each of which may contain one or more test tubes or, in one particular situation to be explained, may intentionally contain no test tubes. In a preferred embodiment, infeed 80 holds as many as 21 racks.

Infeed 80 uses a bidirectional "walking beam" mechanism mounted above a chassis 57 (FIG. 1A) to move racks within infeed 80 and outfeed 100 and to move racks 60 to and from cross-feed 95. The walking beam mechanism is somewhat similar to the mechanism for moving racks 60 in input and output queues as described in U.S. application Ser. No. 08/822,585, filed Mar. 20, 1997, now U.S. Pat. No. 5,861,563, and commonly assigned to the Bayer Corporation, which is incorporated by reference herein. However, among various differences, in infeed 80 of the present invention, the walking beam mechanism has walking beams that are of substantially equal height to stabilize racks 60. Moreover, in the present invention, the walking beam mechanism moves racks 60 generally to the rear of infeed 80, rather than to the front, by moving infeed tray 120, in which racks 60 are placed, sequentially in an upward motion, followed by a rearward motion, a downward motion and a forward motion.

Figure 1B:
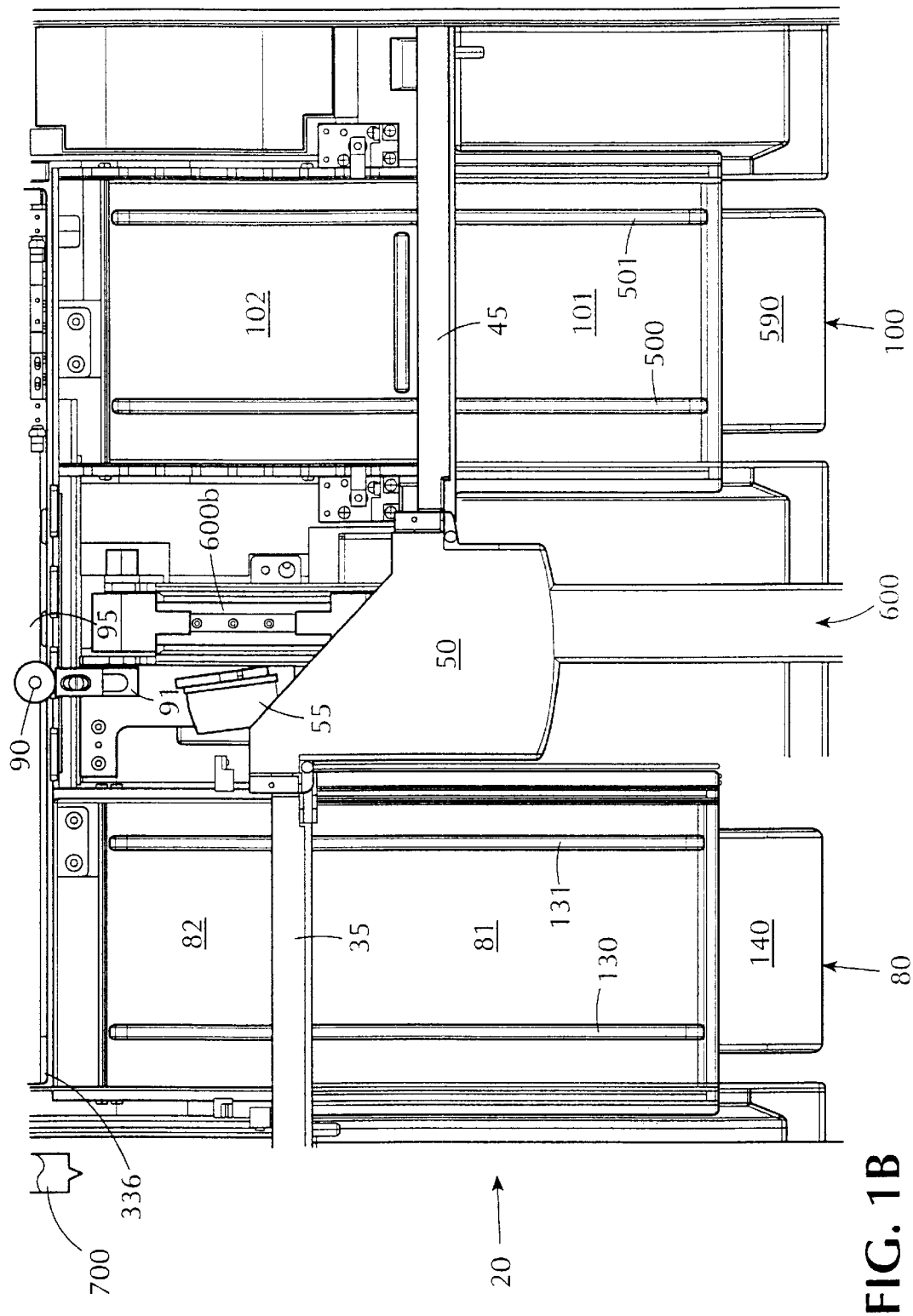
FIG. 1B is a top view of the sample handler of FIG. 1A.
Figure 1C:
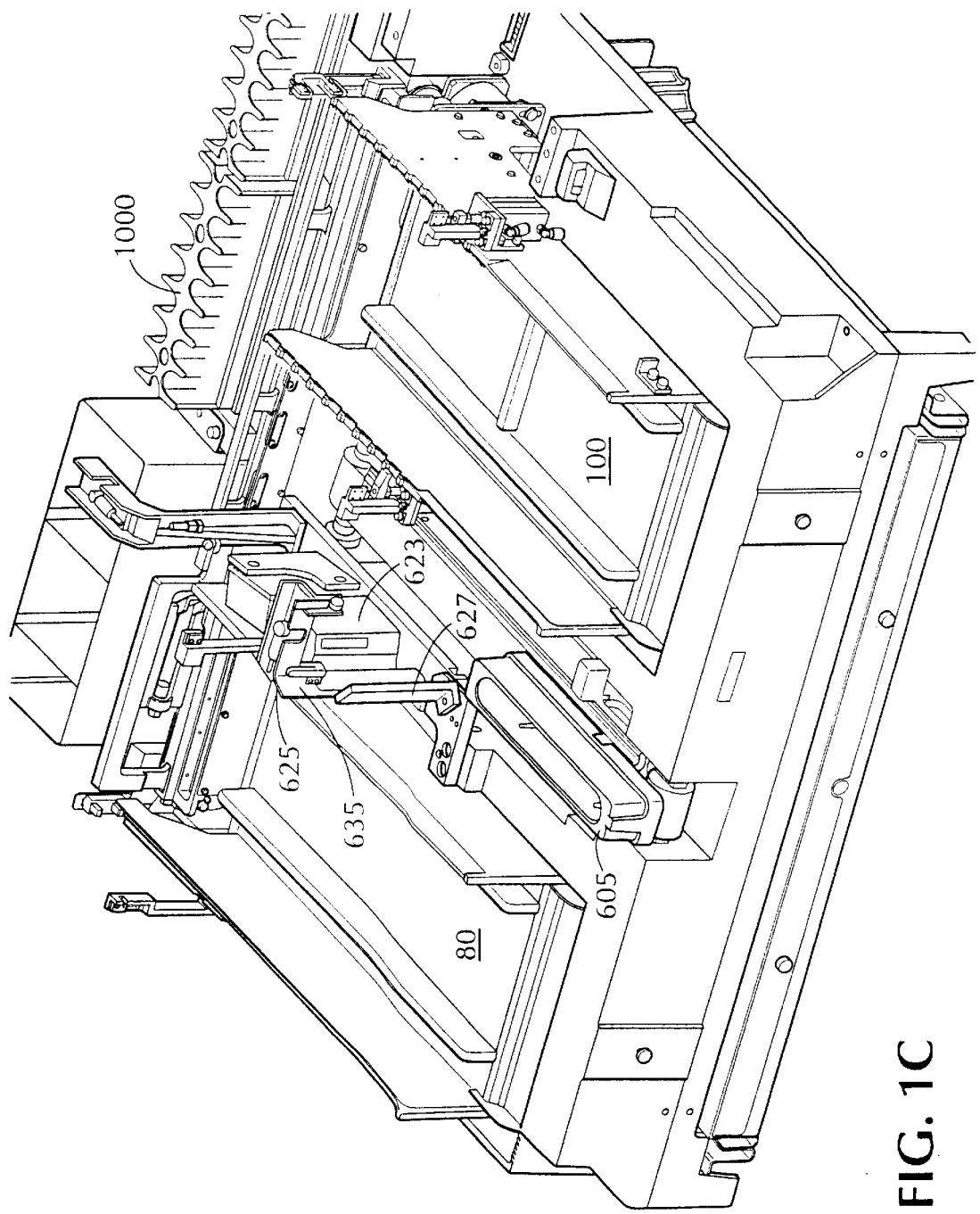
FIG. 1C is a perspective view of the sample handler of FIG. 1A without the panels and doors of the instrument situated above the sample handler.
Figure 2A:
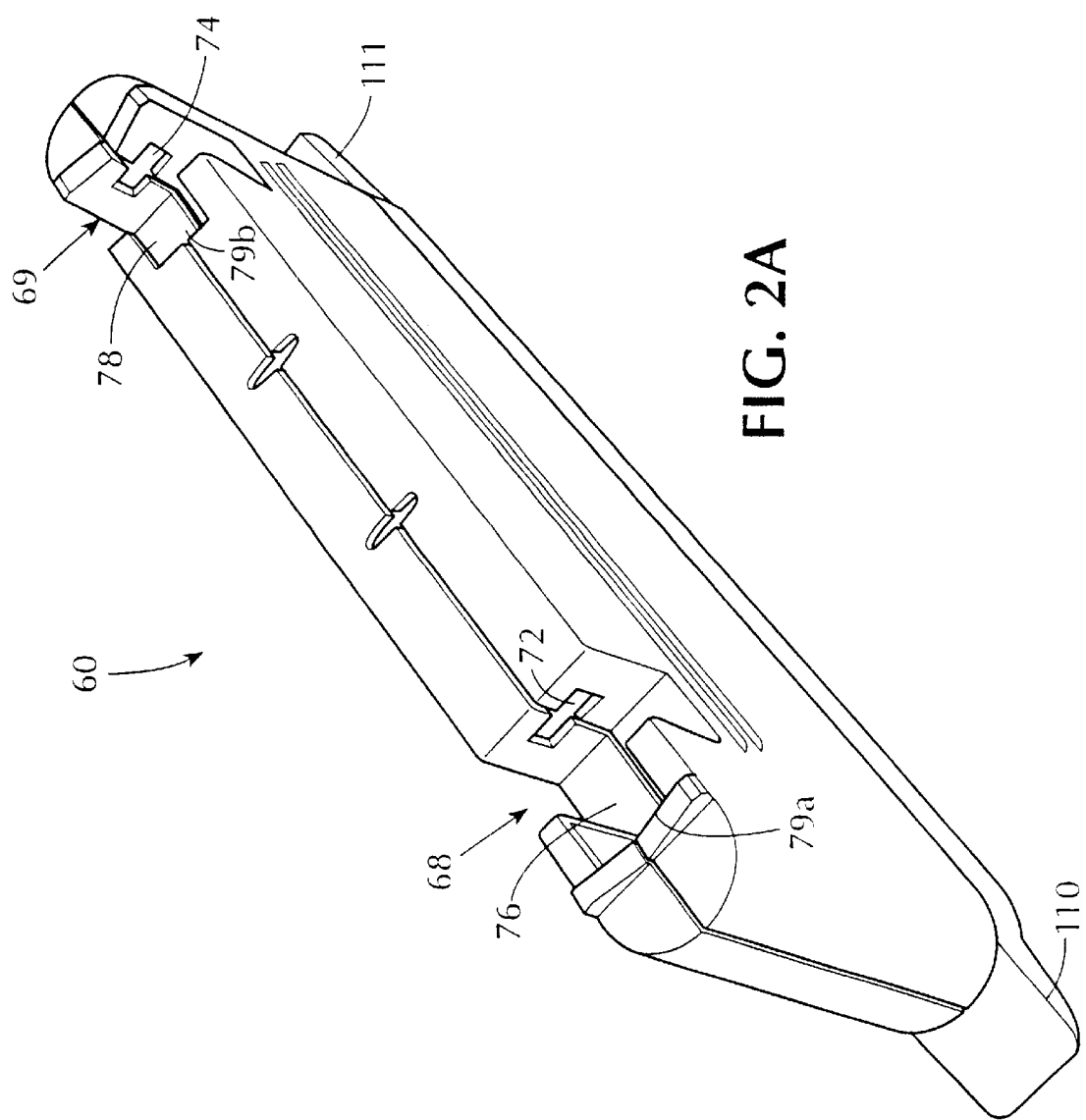
FIG. 2A is a perspective view of the bottom of the test tube rack.
Figure 2B:
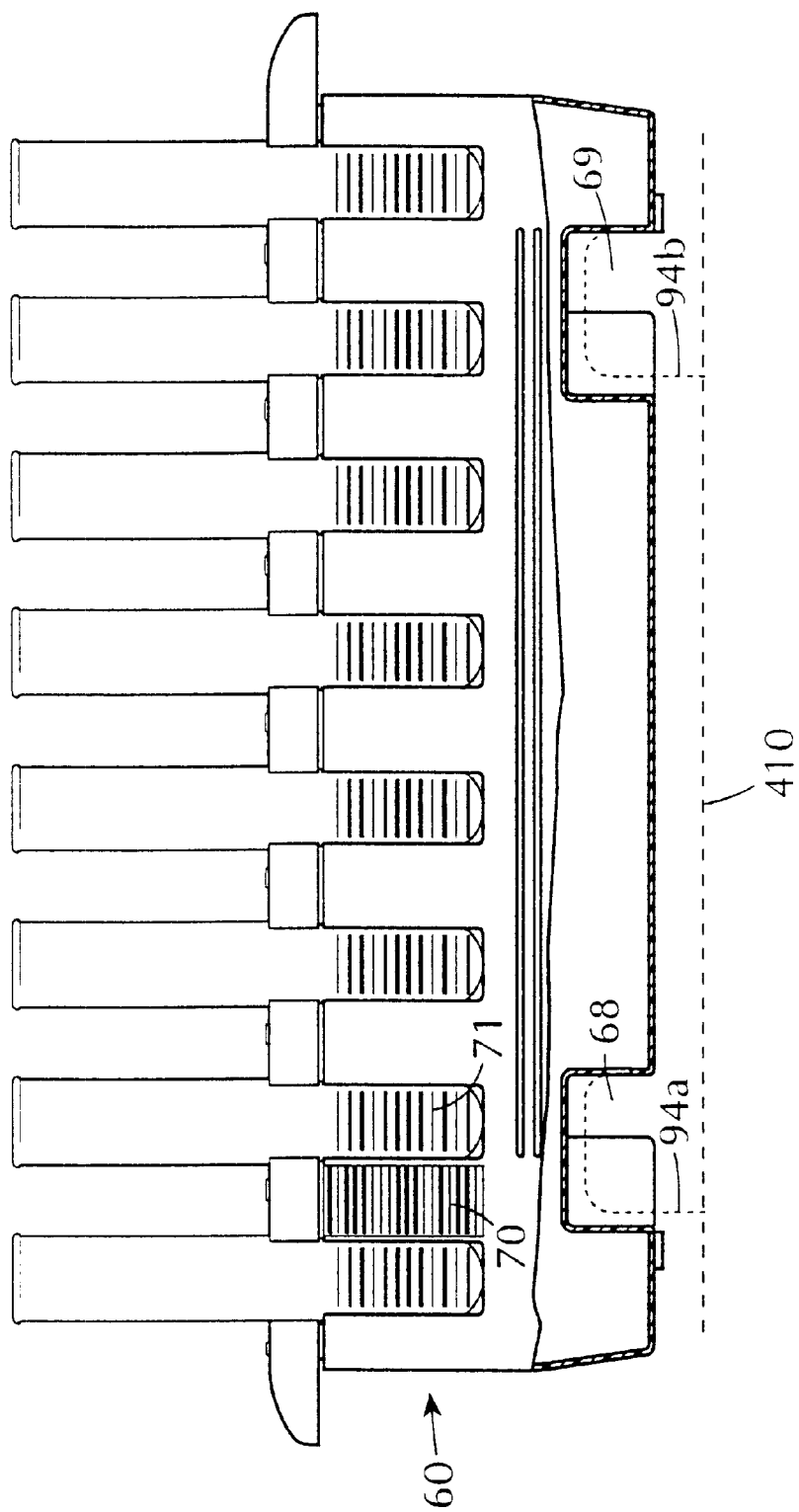
FIG. 2B is an elevational view of the rack holding test tubes and of the pusher fingers, shown in dotted lines, positioned within openings on the bottom of the rack after the rack is placed onto the cross-feed track behind the infeed.
Figure 4A:
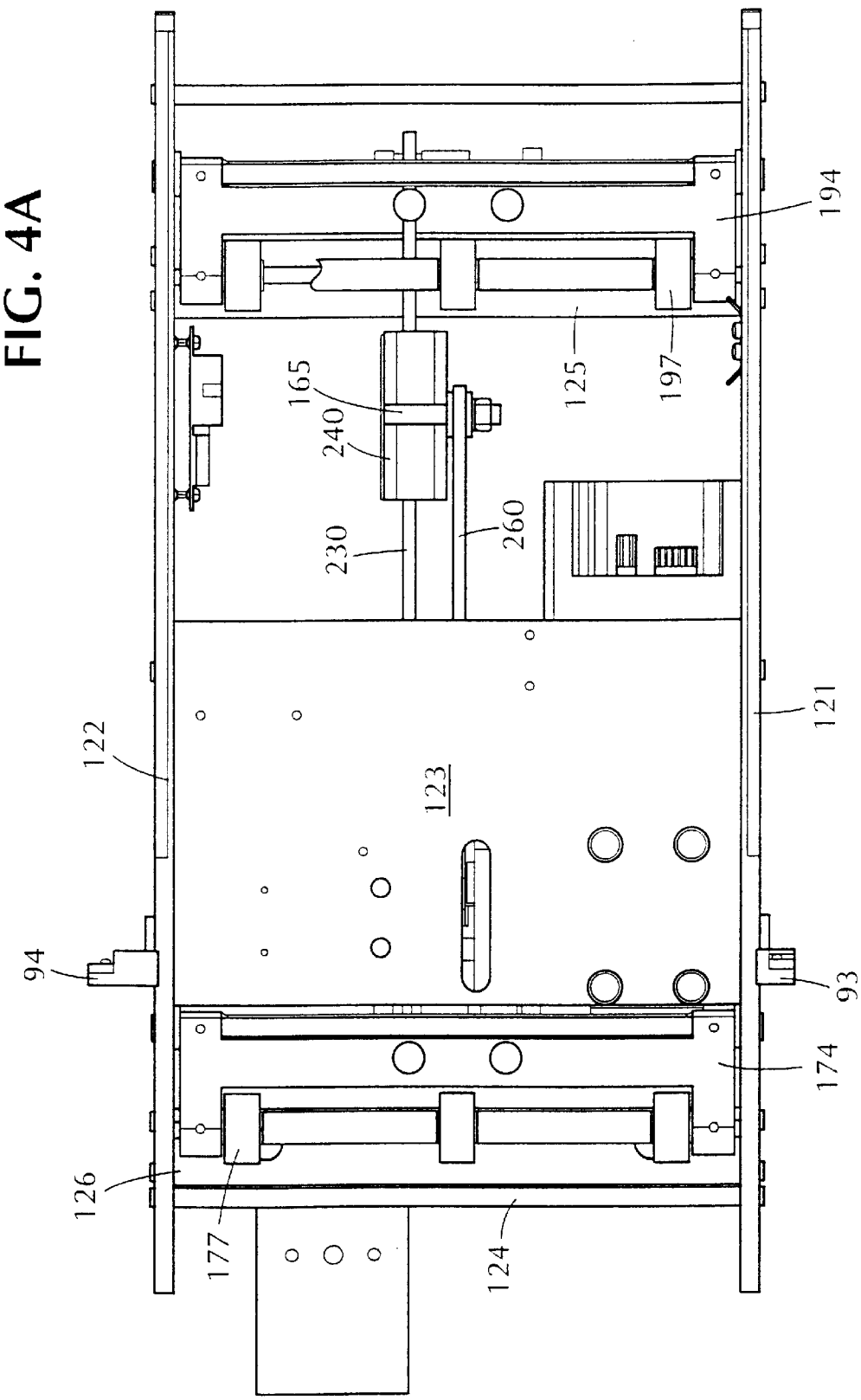
FIG. 4A is a top view of the infeed with the tray removed.

FIG. 4A illustrates infeed 80 with infeed tray 120 removed. Infeed 80 comprises two parallel side walls 121, 122 connected together with cross-beams, such as beams 123–126. Side walls 121, 122 are of equal height so that tabs 110 on racks 60 may hang from the top rims of respective side walls 121, 122. Infeed 80 has no front and rear walls to permit easy insertion of racks 60 into infeed 80 and the transfer of racks 60 to cross-feed 95. A drip tray 140 is attached to the front of infeed 80 to catch spills. (FIG. 1B)

Figure 5C:
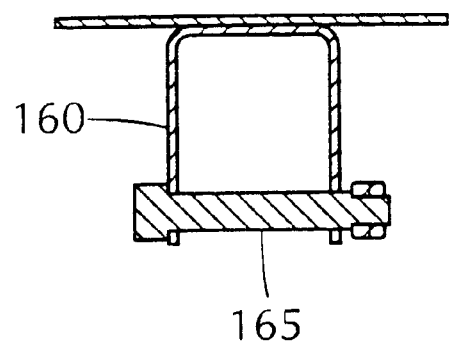
FIG. 5A is a top view of infeed tray.
FIG. 5B is a side view of infeed tray.
Figure 5A:
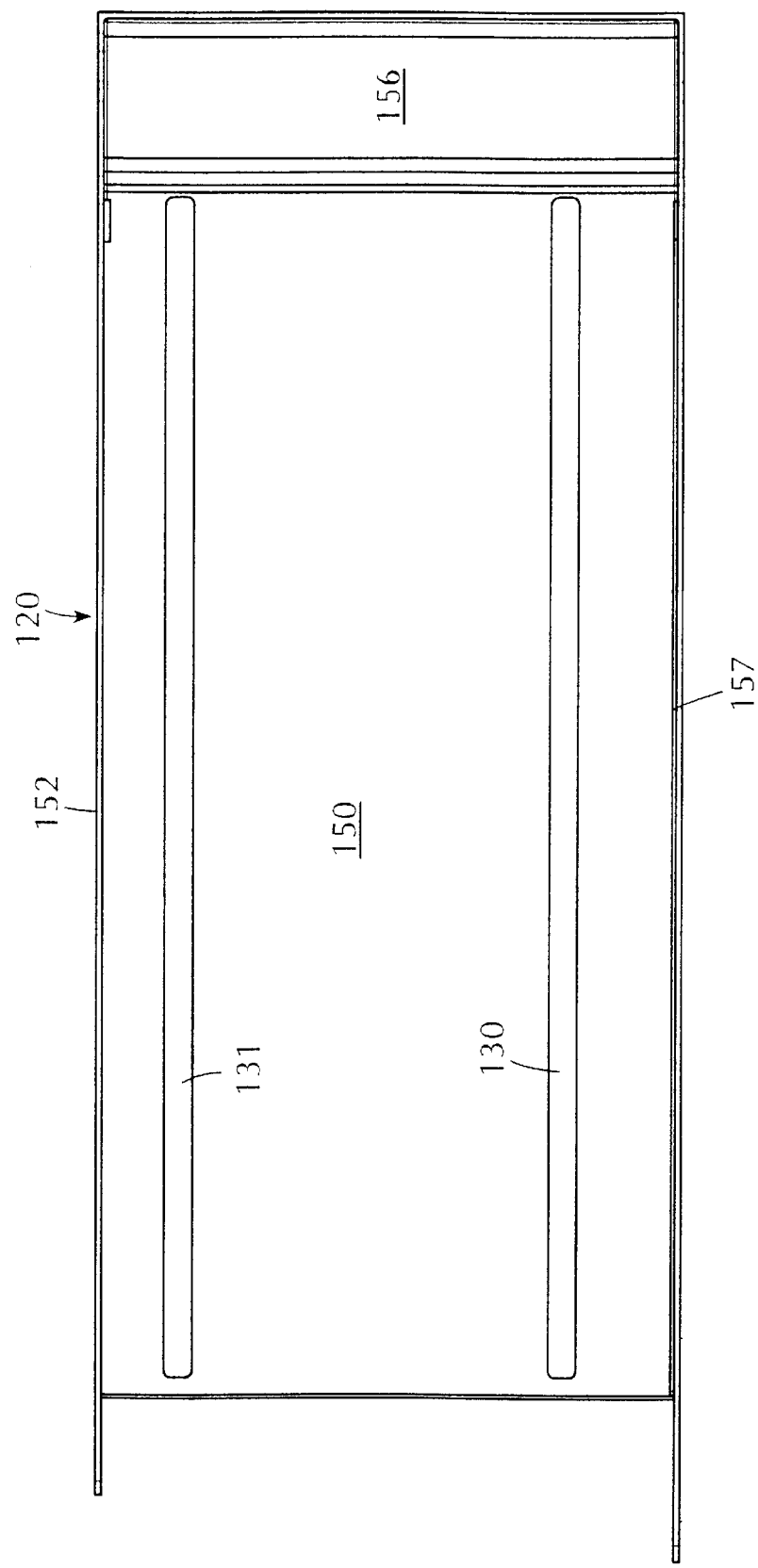

Referring to FIGS. 5A–5C, infeed tray 120 is a movable tray placed in infeed 80. Tray 120 has a bottom 150 and side walls 151, 152 (the "walking beams") but is open at its front and rear like infeed 80 so as not to obstruct the front and rear openings of infeed 80. A middle section 153 on the rear of each of side walls 151, 152 slopes toward the front of tray 120 and the bottom section 154 of side walls 151, 152 then drops vertically to meet bottom 150. Thus, the tops of side walls 151, 152 extend above cross-feed 95 as tray 120 moves rearward above cross-feed 95 without tray 120 hitting cross-feed 95. This also results in the rearmost racks in tray 120 not being positioned above the bottom 150 of tray 120 as they reach the back of tray 120. A short lip 155 projects upward at the rear of tray 120 to contain spills without impeding the movement of racks 60 out of the rear of infeed 80 and a drip tray 156 is attached to the front of tray 120.

Side walls 151, 152 are slightly lower, by approximately 1½ mm in the preferred embodiment, than, and do not overlap the tops of, side walls 121, 122 of infeed 80 when the walking beam mechanism is in the home position. The width of infeed 80 and tray 120 must be somewhat larger than the width of racks 60 such that some skewing of the racks 60 will not cause racks 60 to cam between side walls 151, 152 of tray 120. A U-shaped bracket 160 is mounted to the bottom of tray 120 and a shoulder screw 165 is mounted within bracket 160.

Two stationary guide rails 130, 131 run from the front to the back of tray 120. Guide ails 130, 131 are each narrower than openings 68, 69 on racks 60 to allow openings to move over guide rails 130, 131. Racks 60 do not actually sit on guide rails 130, 131 or on the bottom of tray 120 but rather, as indicated above, are suspended above the bottom of tray 120, hanging from tabs 110, 111 which rest either on the top of side walls 151, 152 of tray 120 or on the top of side walls of infeed 121, 122. Openings 68, 69 on racks 60 key with guide rails 130, 131 to guide racks 60 along infeed 80 while preventing them from skewing or twisting more than slightly within infeed 80. Openings 68, 69 leave adequate clearance for racks 60 to pass over guide rails 130, 131 to permit some skewing so the operator does not have to insert racks 60 into infeed 80 with extreme precision. These features on tray 120 and racks 60 are significant because racks 60 may contain uncapped test tubes whose contents may spill if racks 60 were not prevented from falling down into tray 120.

As explained above, guide rails 130, 131 are situated asymmetrically along the width of tray 120 to insure that racks 60 may only be inserted into infeed 80 in a proper orientation with front wall 61 of each of racks 60 facing the operator to expose bar code labels 70, 71 of racks 60 and each test tube on racks 60 to bar code reader 55. As a result, the operator is intuitively guided by guide rails 130, 131 to not insert racks 60 in the reverse orientation. The top rims of side walls 151, 152 of tray 120 are smooth so that the operator may slide racks 60 freely towards the back of infeed 80 or toward the front of infeed 80 when racks 60 are still in front area 81 which is accessible to the operator.

The walking beam mechanism is shown in FIG. 4B with tray 120 removed and with various other components, including right wall 122 of infeed 80 and cross-beam 123, cut away to show more clearly how the walking beam mechanism operates. A first lift bar 170 is mounted toward the rear of infeed 80. Lift bar 170 comprises a rod 172, the ends of which sit in holes in each of side walls 121, 122 and which defines a first pivot axis around which lift bar 170 pivots, an I-shaped bar 174 and a second rod 176 to which three rollers 177, one roller adjacent each end of I-shaped bar 174 and one roller midway between the ends of I-shaped bar 174, are mounted. A plastic tubular spacer 173 surrounds second rod 176 and keeps rollers 177 spaced at the desired intervals. Second rod 176 may move up and down in a slot 178 on each of side walls. (Only slot 178 on left wall 121 is shown but the slot on right wall 122 is identical.) A third rod 179 is connected between a bracket 180 on the bottom of lift bar 170. A roller 182 is mounted to third rod 179 below the pivot axis of lift bar 170.

A second lift bar 190 is mounted toward the front of infeed 80. This lift bar 190 also comprises a rod 192, the ends of which sit in holes in each of side walls 120, 121 and which defines a second pivot axis around which second lift bar 190 pivots, an I-shaped bar 194 and a second rod 196 to which three rollers 197, one adjacent each end of I-shaped bar 194 and one midway between the ends of I-shaped bar 194, are mounted. A second plastic tubular spacer 193 surrounds second rod 196 and keeps rollers 197 spaced at the desired intervals. Second rod 196 may move up and down in a slot 198 on each of side walls 121, 122. (Only the slot on left side wall 121 is illustrated.) A third rod 199 is connected between bracket 200 on the bottom of second lift bar 190 but no roller is mounted to third rod 199. A long link 230 serves as a tie rod connecting third rod 199 on front lift block 190 to third rod 179 on rear lift block 170, thereby driving second lift bar 190 in synchronization with first lift bar 170.

A motor 210, preferably a single gear brushless DC motor, is mounted in front of rear lift bar 170. Motor 210 has integrated control electronics that interface to the sample handler controller. A disk cam 220, having a profile as shown in FIG. 10A, is mounted to a drive shaft on motor 210 at the center of cam 220. Cam 220 is coupled to roller follower 182 on lift bar 170.

Figure 4C:
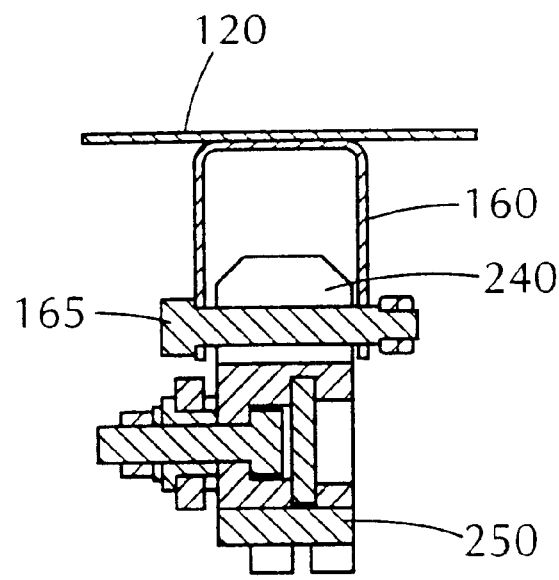
FIG. 4C is a cross-sectional view along line C—C of FIG. 4B of the slider block of the walking beam mechanism with a shoulder screw of infeed tray, shown in FIG. 5C, rested within a channel of the slider block.

A slider block 240 slides above long link 230 and is trapped around long link 230 with a keeper plate 250 mounted to slider block 240 beneath long link 230 (FIG. 4C). One end of a second, shorter link 260 mounts to the left side of slider block 240, generally toward the rear of slider block 240 to minimize the length of short link 260 and not interfere with the placement of tray 120 within infeed 80 by the pulling slider block 240 rearward over long link 230. Where sample handler 20 is designed to accommodate racks 60 according to the preferred embodiment, in which racks may be moved 25 mm per cycle of the walking beam mechanism, the opposite end of short link 260 mounts to the right side of cam 220 at a point 12½ mm away from the center of cam 220 so as to cause tray 120 to advance 25 mm toward the rear of infeed 80 with a 180° turn of cam 220. The precise amount of rearward movement of racks 60 caused by each rotation of cam 220 is not significant in infeed 80 as long as racks 60 move relatively quickly toward the rear of infeed 10.

A channel 270 running sideways through the center of slider block 240 provides a means for locating tray 120 within infeed 80 by inserting shoulder screw 165 into channel 270. U-shaped bracket 160 fits around the sides of slider block 240 and helps to locate and stabilize tray 120. When tray 120 is inserted in infeed 80, with the walking beam mechanism turned off, the top of side walls 151, 152 of tray sit preferably 1½ mm below the top of side walls 121, 122 on infeed 80.

With tray 120 positioned within infeed 80 and sitting in its proper position on slider block 240, the operator may place one or more of racks 60 into infeed 80. A long-range ultrasonic sensor 280 is positioned on cross-feed 95 behind infeed 80. Range sensor 280 emits ultrasonic waves that travel toward the front of infeed 80. Racks 60 are made from a material that reflects an echo back toward range sensor 280 if racks 60 are inserted into infeed tray 120. An emitted wave that is reflected back to and detected by range sensor 280 as an echo signals that one or more racks are in tray 120.

Range sensor 280 may point directly toward the front of infeed 80 but does not in the preferred embodiment because it may be desirable to position other components of instrument 10 behind cross-feed 95 and because it is desirable to also use range sensor as a skew sensor as well to determine if the right side of a rack has been placed on cross-feed 90 skewed away from sensor 280. Therefore, in the preferred embodiment, range sensor 280 is positioned sideways along the axis of cross-feed 95 pointing toward outfeed 100 and into a custom-designed acoustic mirror 290 which is mounted to the back wall 332 of cross-feed 95 and which is off-center to the right side of infeed 80. Acoustic mirror 290, a plastic passive reflector, is constructed from polycarbonate, or any plastic that has a reflective surface.

A preferred range sensor 290 is manufactured by Cosense Sensors Inc. of Hauppauge, N.Y. as Model No. 123-10002. That sensor is enclosed in a shielded body that is 0.425" diameter by 0.75" long. Where the sensor emits a wave at a preferred frequency of 0.5 MHz for 150 milliseconds to have a sufficient range to detect racks 60 inserted at the front of infeed 80, the dead zone, which equals the distance from sensor 280 in which the 0.5 MHz wave cannot be sensed is approximately 2 inches. (The length of the dead zone equals the distance the wave travels before range sensor 280 resumes listening for an echo from the wave.) Therefore, acoustic mirror 290 is approximately 2.5 inches long in the preferred embodiment. The leftmost 2 inches 292 of acoustic mirror 290 accounts for the dead zone within which movement directly within acoustic mirror 290 in front of range sensor 280 cannot be detected. A 0.5 inch angled portion 294 on the right of acoustic mirror 290 has a reflective surface which is angled at a 45° angle toward the front of infeed 80. This bends by 90° the wave emitted by sensor 280 after it has passed the dead zone and focuses the wave toward the front of infeed to detect the presence of racks in tray 120.

In order to best detect a skew of the right side of a rack in cross-feed 90 while performing range sensing, acoustic mirror 290 should be mounted on cross-feed 90 behind infeed 80 with a bias to the right side of infeed as much as possible but the angled portion 294 should be positioned so as to reflect wave toward the front of infeed 80 between guide rails 130, 131.

Software in instrument 10 may determine the distance of the object from the rear of cross-feed 95 based on the time it takes for the sound to be reflected back to range sensor 280. However, there is no need for the software to track the precise position at which the rack that triggers the walking beam mechanism is inserted, although software could be included to determine this information. If range sensor 280 is configured and operated to detect objects beyond the front of infeed 80, the software may also be programmed to reject signals detected by sensor 280 that are generated by objects more than a certain maximum distance from acoustic mirror 290, such as a person walking in front of the infeed 80, to prevent the activation of the walking beam mechanism by signals outside of infeed 80.

The walking beam mechanism is activated by the detection by range sensor 280 of racks 60 in infeed 80, unless there is a rack in the infeed side of cross-feed 95. Upon activation of the walking beam mechanism, cam 220 begins rotating and rolling against roller follower 182, causing lift bar 170 to pivot about rod 179 with rod 176 moving upward within slot 178. Because front lift bar 190 is linked to rear lift bar 170 via long link 230, the pivoting of rear lift bar 170 also causes front lift bar 190 to pivot in the same direction. This causes tray 120 to move upward a total of 3 mm with the top of side walls 121, 122 of tray 120 raised 1½ mm above the top of side walls 151, 152 of infeed 80 when tray 120 is fully raised. As tray 120 moves upwards, tabs 110 on each of racks 60 are picked up off the top of side walls 121, 122 of infeed 80 and transferred onto the top of side walls 151, 152 on tray 120. In the event that range sensor 280 fails and does not activate the walking beam mechanism, the walking beam mechanism may be manually activated. The speed at which the walking beam is preferably activated is 25 rpm +/−2 rpm. This speed, as well as the lift of cam 220 is selected to minimize the noise generated by the transfer of racks 60 between side walls 121, 122 and side walls 151, 152. The position of the walking beam mechanism for infeed 80 (and for outfeed 100) is controlled by activating motor 210 for a given time at a known speed.

As tray 120 nears completion of its upward motion and after racks 60 have been transferred to the top of side walls 151, 152 on tray 120, short link 260 pulls slider block 240 rearwards, as provided for by the positioning of the mounting of short link 260 to cam 260, thereby moving tray 120 with racks 60 rearwards approximately 25 mm. Cam 220 begins lowering lift bars 170, 190 as tray 120 nears completion of its rearward movement, thereby lowering tray 120. As the top of side walls 151, 152 of tray 120 move below the top of side walls 121, 122 of infeed 80, tabs 80 on racks 60 are again transferred from being supported on the top of side walls 151, 152 of tray 120 to the top of side walls 121, 122 of infeed 80. As tray 120 is lowered, cam 220 causes slider block 240 to move tray 120 toward the rear of infeed 80 approximately 25 mm to return tray 120 to its original position. As long as the walking beam mechanism is activated, tray 120 continues moving in accordance with the up-rear-down-forward directions with racks 60 being passed back and forth between the top of side walls 121, 122 and the top of side walls 151, 152. This multidirectional motion of tray 120 causes racks 60 to move rearwards in infeed 80, with some racks 60 pushing the racks 60 behind them backwards toward cross-feed 95 to compact the racks 60 in the rear of infeed 80. Thus, even if racks 60 were placed into tray 120 somewhat skewed, the compacting motion will make them parallel to side walls 151, 152 of infeed tray 120.

Vertical panel 30 covering the front of instrument 10 is positioned above infeed 80 and extends downward to limit operator access to rear area 82 of infeed 80. Panel 30 provides clearance for the tallest test tubes with the tallest caps which are properly seated in racks 60 and gives a visual cue to the operator to reseat any improperly seated test tubes. Infeed 80 has a front area 81 in front of panel 30 which is accessible to the operator and, although rear area 82 is not accessible to the operator, the operator could push racks 60 in front area 81 toward rear area 82, causing racks 60 in rear area to be pushed backward. The operator may remove a rack 60 or shuffle the order of racks 60 before they pass behind panel 30 above infeed 80.

Test tubes on racks 60 must be seated properly in racks 60 by the operator not only to insure the stability of the test tubes but also to position bar code labels 71 on test tubes so they may be read by bar code reader 55 along cross-feed 95, and to insure that the test tubes may pass under the armature 91 for ultrasonic liquid level sensor 90 extending above cross-feed 95 so that the level of liquid in the test tubes is properly determined by the ultrasonic liquid level sensor 90.

Figure 3B:
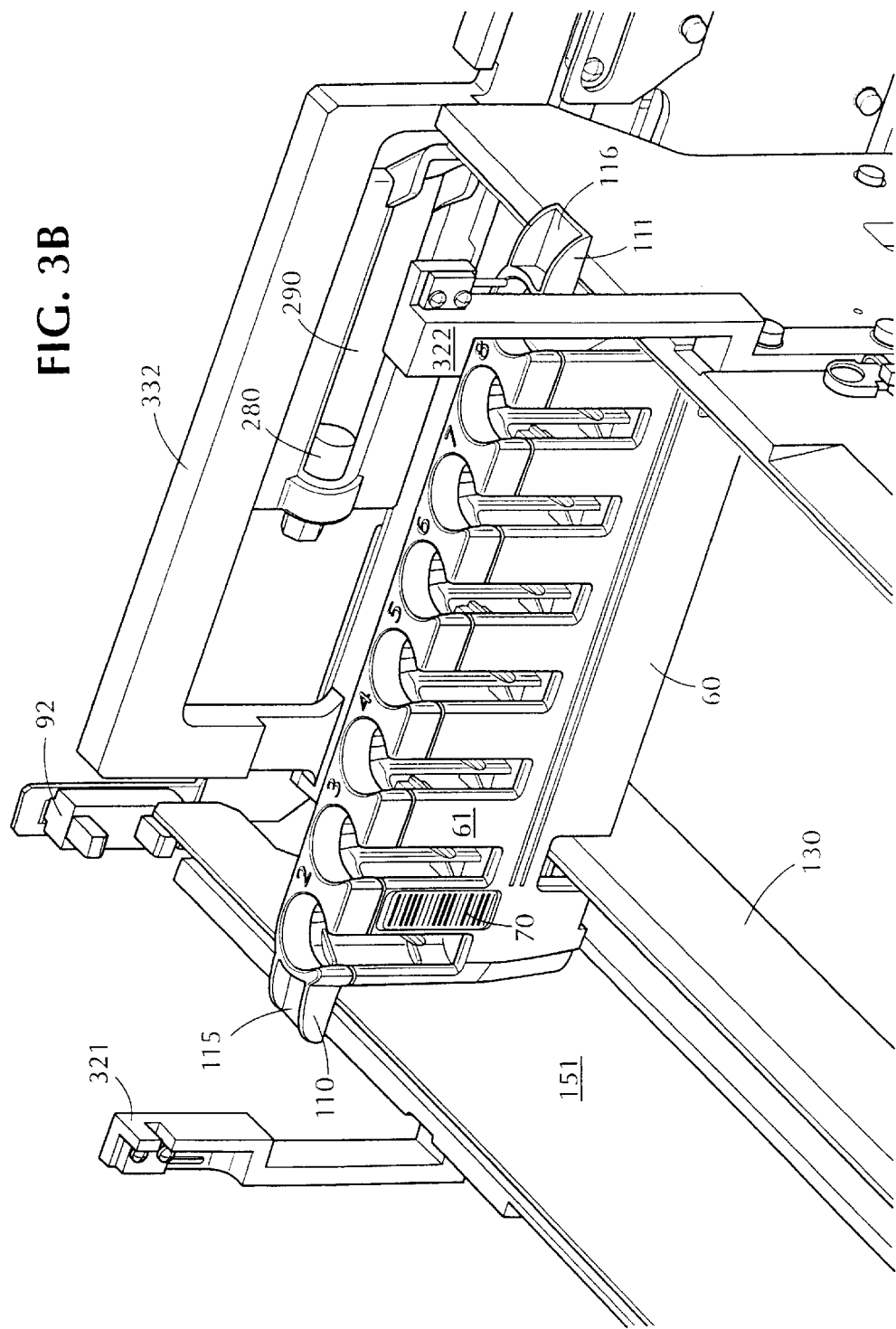
FIG. 3B is a perspective view of portions of the infeed and cross-feed with a test tube rack in a rear area of the infeed that is not accessible to the operator.

A gross height sensor 320 may be optionally mounted to the side of infeed 80 behind panel 30 to detect test tubes that are not fully seated but pass under panel 30 or whether some test tubes are taller than the specifications of instrument 10 permit it to handle. Gross height sensor 320 comprises an optical infrared through-beam sensor 320 having a transmitter and receiver mounted on brackets 321, 322, respectively, and should be calibrated to be sensitive enough to detect clear glass test tubes. Bracket 321 for the transmitter for gross height sensor 320 is mounted on one side of infeed 80 and bracket 322 for the receiver is mounted to the opposite side, both being mounted so that the transmitter and receiver detect test tubes positioned at a height slightly higher than the tallest expected test tube with a cap to be placed in sample handler 20 with tray 120 fully raised. If gross height sensor 320 detects that a particular test tube in a rack is seated too high, the movement of the walking beam mechanism for infeed 80, which causes racks 60 to move toward the rear of infeed 80, is stopped and the walking beam mechanism is activated in the reverse direction (cam 220 causes tray 120 to move back, up, forward, down) to move the rack with the improperly seated test tube back into the operator accessible from front area 81 of infeed 80 to enable the operator to reseat the test tube or to transfer a sample in a test tube which is too tall for instrument 10 to a test tube which meets the specifications. An empty rack (which normally would be filled with one or more test tubes) is shown in FIG. 3B in a position after it has passed panel 30 and gross height sensor 320.

The walking beam mechanism continues cycling and moving racks 60 rearward to the back of infeed 80 until at least one of racks 60 reaches the back of tray and the cycling of tray 120 lifts the rearmost rack 60 in infeed 80 and transfers it onto a stationary track 336 that is formed around the inside perimeter of cross-feed 95 (the distance separating the rear of infeed 80 from track 336 being preferably approximately 25 mm) where cam 220 causes a rearward movement in a single cycle of 25 mm (FIGS. 1B and 6B). FIG. 3C shows the rack seated in cross-feed 95. This transfer to cross-feed 95 is detected by the left tab 110 of rack being placed on sensor 92 so as to block the infrared beam on optical sensor 92. Once rack is moved to cross-feed 95, the walking beam mechanism cycles two additional times, which causes chamfered edges 157 on the top rear of tray 120 (FIG. 5B) to hit the front of tabs 110, 111 and thereby pushes the rack rearward before catching the tabs 110, 111 on side walls 151, 152 and again placing the rack on track 336. This insures that the rack on track 336 of cross-feed 95 is perpendicular to cross-feed 95. The walking beam mechanism then turns off.

The walking beam mechanism will automatically stop sooner if a rack is not deposited in cross-feed 95 after a certain amount of time, during which the walking beam mechanism is cycled a maximum number of times. This would indicate that the movement of racks 60 has probably been obstructed. In the embodiment where the walking beam mechanism moves racks 60 25 mm per cycle and tray 120 holds 21 racks each 23 mm wide, the cycling may be automatically stopped after a time sufficient for the walking beam mechanism to cycle 25 times because only 21 cycles should have been necessary to move a rack inserted at the front of tray 120 to cross-feed 95.

During the operation of the walking beam mechanism, the operator may insert additional racks 60 into infeed 80 even though tray 120 is moving. The operator may also push racks 60 toward the rear of infeed 80 as far as possible without disturbing the operation of sample handler 20.

As explained above, in addition to detecting racks 60 in tray 120, range sensor 280 also assists in detecting if a rack 60 is inserted into cross-feed 95 by tray 120 is skewed. Only limited skewing is possible due to guide rails 130, 131 in tray 120 which transfers rack to cross-feed 95. however, a high degree of accuracy is required when a rack is placed on cross-feed 95 because test tubes must be properly positioned to be removed by a robotic arm (not shown). The proper placement of the left side of a rack into cross-feed 95 is detected by left tab 110 on the rack being placed above sensor 92. At the same time, range sensor 280 detects if the right side of rack is skewed by calculating that readings across range sensor 280 are within a small limited allowable range away from range sensor 280, the maximum limit preferably being 0.1 inches. The rack is determined to be skewed if the right side of rack is further than this maximum limit.

Homing means, such as those known to those skilled in the art, should be provided to accurately home the walking beam mechanism for infeed 80 (and for outfeed 100).

Cross-Feed

Cross-feed 95 is designed to firmly grab racks 60 placed on track 336 of cross-feed 95 by the walking beam mechanism of infeed 80, one rack at a time, to push the rack linearly to the opposite side of cross-feed 95 behind outfeed 100, and to hold that rack downward and as vertically as possible to both position each test tube in one of the eight predetermined registration positions on cross-feed 95, which the robotic arm recognizes, to allow a robot to remove test tubes individually, without disturbing other test tubes in the rack 60, and without accidentally pulling up the rack along with the test tube due to friction between the test tube and the rack. Once the test tubes have been removed from the rack 60, outfeed 100 removes the rack from cross-feed 95

Referring to FIGS. 6A–6E, in addition to track 336, cross-feed 95 has a front wall 330, a rear wall 332 (or fence), a linear transport mechanism 335 positioned under track 336 and a rack transport connector subassembly that comprises a platform 410 connected to the top of linear transport mechanism 335 for gripping the rack on cross-feed 95. Front wall 330 is short where it is situated behind infeed 80 and outfeed 100 to provide clearance for a rack to be placed on cross-feed 95 by infeed 80 and to be removed from cross-feed 95 by outfeed 100. The center portion of front wall 330 that is not located behind infeed 80 or outfeed 100 is taller and has a preloading means for providing a force against the front of the rack as it moves through cross-feed 95 to maintain the perpendicularity of the rack to track 334. However, this center portion is lower than the level of openings 63 on rack to permit the reading of bar code labels 70, 71. In one embodiment, the preloading means comprises four pressure springs 336 on the back of front wall, each comprising a short metal link 337 parallel to front wall 330 and a spring 338 between each end of link 337 and mounting points 339 on front wall 330. Rear wall 332 also helps properly seat the rack on cross-feed 95 perpendicularly to track 336. Rear wall 332 is raised in the area behind infeed 80 to prevent rack 60 from tilting backwards as it is passed by tray 120, when tray 120 is a raised position, to cross-feed 95.

The linear transport mechanism of cross-feed 95 comprises two pulleys 340, 341, one pulley mounted to each end on a bottom 334 of linear transport mechanism 335, and a belt 345 surrounding pulleys 340, 341. The linear transport mechanism is driven by a stepper motor 350, that is preferably controlled by the microprocessor in the cross-feed controller, located beneath belt 345 behind the outfeed 100 side of sample handler 20. Stepper motor 350 is electrically coupled to the cross-feed controller. The gear head output shaft 360 on motor 350 is coupled to a pulley 370 which is in turn coupled to pulley 341 with drive belt 380. A rail 390 is mounted along the top of assembly bottom 334 on linear transport mechanism 335 and extends between pulleys 340, 341. Two bearing blocks 400, 401, which may be any bearing block that fits, slide along guide way 390 and are also attached to and move with belt 334. A platform 410 is mounted to bearing blocks 400, 401.

Two L-shaped pusher fingers 94a, 94b are pivotally mounted at pivot points 427 to the top of platform 410 and each of fingers 94a, 94b is preloaded with a spring 405a, 405b (FIG. 6H) to a raised position. The upper ends of pusher fingers 94a, 94b are angled upward towards the outfeed 100 side of cross-feed at an angle in the approximate range of 20–45° to cam into windows 72, 74 on racks 60 and the top end 425 of each of fingers 94a, 94b is chamfered on both front and back sides to bias the rack against track 336. The back chamfer on fingers 94a, 94b also biases the rack 60 against rear wall 332 to ensure that the test tubes are properly in the registration locations for robot access.

A rack 60 may be placed in cross-feed 95 when platform 410 is positioned under the arriving rack. In this case, with platform 410 in position behind infeed 80, pusher fingers 94a, 94b are in the raised position and fit within openings 68, 69 without contacting windows 72, 74. At other times, a rack 60 may be placed by tray 120 on cross-feed 95 when platform 410 is still holding another one of racks 60 behind outfeed 100 or returning from the opposite side of cross-feed 95. In this case, as platform 410 moves under the rack 60 behind infeed 80, pusher fingers 94a, 94b are pivoted downward to the right by the force of the rack and then return to the raised position as they arrive within openings 68, 69.

Once a rack is placed securely on cross-feed 95, i.e. after it has been placed on cross-feed 95 and two additional 360 degree movements of cam 220, platform 410 begins moving to the opposite side of cross-feed 95 and, in the process, pusher fingers 94a, 94b cam within windows 72, 74, respectively, to push the rack across track 336. The rack should not accelerate to more than approximately 0.3 g to avoid spilling the liquid in open test tubes.

Bar code reader 55 is mounted adjacent cross-feed 95 a short distance beyond the inner side of infeed 80 and reads bar code labels 70, 71 on the rack and test tubes as rack and test tubes are transported along cross-feed 95 in front of bar code reader 55. If a label cannot be read, such as when the bar code label on the test tube is not oriented toward bar code reader 55, the test tubes which were not identified are not extracted from the rack for processing by instrument 10 (or are sent to the stat shuttle 600 for a second attempt at container identification).

An ultrasonic liquid level sensor 90 is positioned above cross-feed 95 within a sensor holder 408 mounted to a bracket 91. (FIGS. 6E–6G) The sensor 90 is preferably mounted in a gimbal 407 that fits within sensor holder 408. A preferred sensor 90 is height sensor ("transponder") manufactured by Cosense as Model No. 123-10001. Sensor 90 should be positioned on bracket 91 approximately 5 inches from the bottom of the rack to allow for a 0.75 inch dead zone immediately beneath sensor 90. The data provided by sensor 90 may be used to provide a profile of the type of test tubes in the rack, the level of liquid in open test tubes, and whether test tubes have a cap which must be removed. The rack is also profiled to provide a height reference. This profiling is the subject of the referenced application entitled Dynamic Noninvasive Detection of Analytical Container Features Using Ultrasound. If the profiling indicates that a cap is present, instrument 10 instructs a robotic arm to transport the capped test tubes to an automatic decapper, which is preferably a component on instrument 10 and may be included in the sample handler module. After the decapper removes the cap, another ultrasonic liquid level sensor (not shown) in the decapper determines the liquid level in the now uncapped test tube.

Ultrasonic liquid level sensor 90 is mounted upstream from bar code reader 55 along cross-feed 95 to provide the necessary distance for the rack 60 on platform 410, which is initially at rest behind infeed 80, to accelerate up to the slew speed that allows ultrasonic liquid level sensor 90 to take a sufficient number of equally spaced data points and profile the test tubes in the rack before passing under ultrasonic liquid level sensor 90. For example, in one embodiment, the required slew speed may be 2 inches/second so ultrasonic liquid level sensor 90 must be placed far enough along cross-feed 95 to allow the rack 60 to reach that slew speed. Profiling requires a smooth motion of the rack and test tubes under sensor 90. Test tubes cannot accelerate too quickly or samples in test tubes will be disturbed.

The data collected by ultrasonic liquid level sensor 90 is also used in conjunction with a homing sensor (not shown) for platform 410 built into the linear transport mechanism of cross-feed 95 to verify that the rack is fully seated.

Track 336 of cross-feed 95 must maintain the perpendicularity of the rack 60, to insure the accuracy of a critical datum point for the height reference set by tabs 110, 111 on the rack as measured by the ultrasonic liquid level sensor 90 and to maintain the registration positions for the robotic arm. Should sensor 90 malfunction, sample handler 20 could still be used but the test tubes would all have to be uncapped and be filled to substantially the same height.

As soon as the rack clears the area of cross-feed 95 behind infeed 80, if additional racks are in tray, they are detected by range sensor 280 and the walking beam mechanism starts cycling again and continues moving until another rack is placed on track 336 of cross-feed 95.

When a rack reaches the opposite side of cross-feed 95, which is the unloading position shown in FIG. 3D for unloading test tubes from rack to be transported elsewhere in instrument 10, the right tab of rack is positioned above sensor 93, which is an optical sensor similar to sensor 92. A hard mechanical stop 440 is also provided at the outfeed end of cross-feed 95 adjacent rail 390 to stop bearing blocks 400, 401 in a precise position for unloading of the test tubes and subsequent transfer of the rack 60 to outfeed 100. Hard stop 440 is adjustable to accommodate some slight variations in the positioning of cross-feed 95 in different instruments. After sensor 93 is triggered, software instructs stepper motor 350 to advance 2 additional steps to tension pusher fingers 94a, 94b to bias the rack against hard stop 440.

While in the unloading position, pusher fingers 94a, 94b remain engaged in windows 72, 74 and a robotic arm located on instrument 10 above sample handler 20 may extract each of the test tubes from the rack. The robotic arm is able to extract test tubes positioned in cross-feed 95 as long as the test tubes are within one of the registration locations. Allowance is made for some slight variation in position. The engaged pusher fingers 94a, 94b mechanically constrain rack during extraction of the test tubes by robotic arm to prevent friction between the test tubes and rack from pulling the rack out of cross-feed 95 along with the test tubes.

An optical through beam sensor (not shown) may be added to cross-feed 90 to detect if there is a rack in the cross-feed during the initialization of instrument 10 after a power outage. Generally, this will not occur if an uninterrupted power supply is attached to instrument 10 to allow an orderly power down, including moving racks 60 out of cross-feed, to insure that no racks in cross-feed 95 remain undetected upon the restoration of power.

Outfeed

Referring to FIG. 3E, rack is moved to outfeed 100 after it has been emptied of test tubes by the robotic arm. Like infeed 80, outfeed 100 comprises a bidirectional walking beam mechanism mounted above the chassis 57 similar to the walking beam mechanism as described and shown in FIG. 4B above with reference to infeed 80 (except that cam 220' has a different cam profile, a preferred profile being shown in FIG. 10B). Outfeed 100 has side walls 510, 511 which are joined together with cross-beams.

Outfeed 100 has a front area 101 which is always accessible to the operation for removing racks from the system and a rear area 102 which is inaccessible to the operator during operation of instrument 10. The operator is prevented from inserting a hand in rear area 102 by panel 40 and door panel 45 (FIGS. 1A and 1B) on instrument 10. A drip tray 590 is attached to the front of outfeed 100 to catch any spills.

Sitting within outfeed 100 is an outfeed tray 450 which has side walls 505, 506 and a bottom 507 but is open at the front and rear of tray 450. (FIG. 7A and 7B) Tray 450 preferably holds a total of 20 racks with 10 racks in rear area 102 and the remaining racks in front area 101. Like infeed tray 120, the top of side walls 505, 506 of outfeed tray 450 extend farther back toward cross-feed 95 than the bottom of side walls 505, 506, sloping forward along a middle section at the rear of side walls 505, 506 so that the bottom 507 of tray 450 does not hit cross-feed 95 when tray 450 rotates backward over cross-feed 95.

Tray 450 has a shoulder screw 460 attached to a U-shaped bracket 461 on the bottom of tray 450 (FIG. 7C) which sits in a channel on sliding block that is identical to sliding block 240 and causes the backwards and forward movements of tray 450. Two guide rails 500, 501 extend from the front to back of the top of tray 450 but are asymmetrically positioned across the width of the tray, with the same asymmetry as in infeed tray 120, to accommodate and prevent skewing of racks 60. Tray 450 is sufficiently wider than racks 60 to prevent camming of racks against side walls 505, 506. Outfeed tray 450 has a lip 580 in the back (FIG. 7B) and a drip tray 600 attached to the front of tray 450 for spill containment.

There are two primary differences between infeed 80 and outfeed 100. The first difference is that the top of side walls 510, 511 on outfeed 100 and top of side walls 505, 506 on outfeed tray in rear area 102 have trapezoidal detents 531–539 (on outfeed side walls 510, 511) and detents 540–549 (on tray side walls 505, 506). Tabs 110 on racks 60 may sit in detents 531–539 and 540–549 in order to precisely position each of racks 60. This allows the robotic arm to locate the tube receptacles in racks 60 to which the test tubes are to be returned using the predefined grid of 72 registration locations where test tubes may be inserted in outfeed 100. The software tracks which of detent positions have racks and which tube receptacle positions in those racks are available for the insertion of test tubes. In the embodiment illustrated in FIGS. 3D–3F, there are nine detents 530 on outfeed side walls 510, 511 and ten detents 531 on side walls 510, 511 of tray 450. When tray 450 is in its rest position in outfeed 100, nine rear detents 540–548 in tray 450 are aligned with the nine detents 531–539 on outfeed 100. Detents 531–539, 540–549 are identical in shape and size. They are approximately 2 mm larger than the width of tabs 110 to provide a small amount of clearance for tabs 110. Thus, where detents 531–539, 540–549 are approximately 25 mm, tabs 110 are made approximately 23 mm wide. While the precise distance that tray 120 in infeed 80 must move rearward to translate racks 60 along infeed 80 may vary, the distance which tray 450 must move must be precise, 25 mm for the preferred specifications, to move racks 60 from one detent to another.

Detents are separated by ridges 550 which maintain a separation between racks 60. Ridges 550 are designed to be high enough to maintain racks 60 in the registration positions within the detents. The cam profile of outfeed 100 must be designed to lift racks 60 high enough and far enough so as to clear ridges 550 when being moved between the detents.

If racks 60 are initially not centered within the detents as they are moved within tray 450, the trapezoidal shape of detents pushes racks 60 into the center of the detents. The trapezoidal shape of the detents and 2 mm clearance also allows racks 60 to "float", ie., tilt slightly forward or backward, when a robotic arm inserts a test tube in a tube receptacle in the rack should the robotic arm or test tube be slightly angled when the tube is inserted in the rack.

The second primary difference between infeed 80 and outfeed 100 is in the cam profile. The outfeed cam causes outfeed tray 450 to be raised and lowered a larger distance than infeed 80, the total distance between the highest and lowest points being preferably 7½ mm. When tray 450 is filly lowered in outfeed 100, side walls 505, 506 sit 4 mm below side walls 510, 511. The cam raises tray 450 3½ mm, so as to lift tray 450 above ridges 550 between detents.

Raising tray 450 higher in outfeed 100 does not create the same problem it would create in infeed 80 because the up and down movement of racks 60 only occurs in the rear area 102 of tray 450, which is enclosed behind panel 40 and therefore is less noisy and disturbing to the operator than the movement of racks in infeed 80 where almost ⅔ of the tray is exposed to the operator.

Outfeed 100 both removes the rack, which has been emptied of test tubes from cross-feed 95 and moves racks 60 from one detent position to a second adjacent detent position closer to the front of outfeed 100 to generally output racks 60 toward the front of outfeed 100. As with the walking beam mechanism on infeed 80, the movement of the walking beam mechanism on outfeed 100 is accomplished by the rotation of tray 450 in conjunction with the transfer of tabs 110, 111 on rack between the top of side walls 510, 511 on outfeed 100 and the top of side walls 505, 506 on tray 450.

To remove a rack 60 from cross-feed 95 after the test tubes have been removed from the rack 60 by the robotic arm, as tracked by the software, the motor on the outfeed walking beam mechanism is activated for a predetermined length of time to rotate the outfeed cam in a counterclockwise direction approximately a quarter of a turn. This causes outfeed tray 450, in a continuous motion, to first move backward approximately 25 mm, which is the distance between two adjacent detents, such that the rearmost detent 540 is positioned under tabs 110, 111 and to thereby capture and cradle the rack between side walls 505, 506 of tray 450. At that point, the outfeed walking beam mechanism momentarily stops for a fixed time and holds tray 450 in a fixed position, while pusher fingers 94a, 94b are extracted from windows 72, 74 on the rack 60 in cross-feed 95, which has been emptied of test tubes, to allow platform 410 to return to the opposite side of cross-feed 95 behind infeed 80. As the platform 410 begins moving, the left side of pusher fingers 94a, 94b contact walls 79a, 79b and are thereby pushed downward to move out from under the rack 60. By cradling the rack as pusher fingers 94a, 94b are extracted from windows, outfeed 100 prevents the rack 60 from returning toward infeed 80 along cross-feed 95. After the timeout for pusher fingers 94a, 94b to clear the rack, the rack 60 is captured within detent 540 on tray 450 and the outfeed walking beam mechanism is again activated, causing tray 450 to move the extracted rack upward approximately 7½ mm, side walls 505, 506 of tray 450 rising approximately 3½ mm above the top of side walls of outfeed 100 and thereby transferring tabs on racks from the top of side walls 510, 511 of outfeed 100 to the top of side walls 505, 506 of tray 450. Tray 450 then moves forward 25 mm and downward 7½ mm, transferring tabs 110, 111 on racks 60 to side walls 510, 511 of outfeed 100, depositing the rack removed from cross-feed 95 into rearmost detent position 531 on outfeed 25 mm closer to the front of outfeed 100.

After removal of the first rack from cross-feed 95, the cycling of the walking beam mechanism on outfeed 100 is repeated to remove other racks 60 after they are emptied of test tubes in cross-feed 95. FIG. 3E shows a rack after it has been moved forward 3 detent positions and is suspended from detent 533. Tray 450 cannot rotate while a rack is in cross-feed 95 behind outfeed 100 before the test tubes are removed from the rack 60 because the rack 60 must remain seated in platform 410 during that time, but cycling resumes after the test tubes have been extracted from that rack 60. As tray 450 picks up a rack 60 from cross-feed 95, it also picks up any other racks 60 in the rear area 102 of outfeed 100 and moves them towards the front of outfeed 100 one detent position at a time. Detent positions 531–539 are generally filled with racks 60 before the frontmost rack is output into the user-accessible area of outfeed 100 when a tenth rack is picked up by tray 450.

Test tubes are output from other modules in instrument 10 after processing and placed in the frontmost rack by robotic arm as they are output until that rack is full of test tubes. After the frontmost rack is filled, the remaining racks are filled with test tubes, with a rack 60 that has an empty tube receptacle 63 and is closest to the front of outfeed 100 being filled first.

In the front area of tray 450, side walls 510, 511 have smooth top rims and the top of side walls 505, 506 have an undercut 560 such that the top of side walls 505, 506 of tray 450 in this front area are always lower than the side walls 510, 511 of outfeed 100, even when tray 450 is fully raised by the walking beam mechanism. This prevents tray 450 from lifting and moving racks which are fed out into front area 101 of the tray. Racks 60 are output into this front area 101 may be manually removed by the operator. If not immediately removed by the operator, the currently-outputted rack pushes and compacts the previously-outputted racks in front area 101 along the smooth rims at the top of side walls 510, 511 toward the operator. A sensor 595 at the front of tray detects if tray 450 is filled with racks and turns off the motor for the walking beam mechanism on outfeed until some of racks 60 are removed. There is no front wall on tray 450 to make it easier to remove racks 60 by the operator sliding one hand under several racks and simultaneously lifting those racks with the other hand.

If a test tube which has been returned to the outfeed 100 is needed by the operator immediately and the operator cannot wait until all nine detent positions 531–539 are filled before the frontmost rack is output, sample handler 20 may be instructed by the operator with software at the user interface of instrument 10 to output the frontmost rack immediately. Upon receiving this instruction, sample handler 20 cycles outfeed 100 to move racks forward toward the front of instrument 10 until the frontmost rack is output and then the walking beam mechanism is cycled backwards in the reverse direction to move racks 60 remaining in rear area 102 of outfeed 100 one at a time back toward cross-feed 95 to their original positions. Undercut 560 on tray 450 prevents racks 60 in front area 570 from being fed backwards into the rear area 102 during this reverse movement of racks back toward cross-feed 95.

As a result of moving some racks 60 with empty tube receptacles 66 out from outfeed rear area 102 to front area 101 for the operator to immediately remove a test tube from a particular rack, there may not be sufficient space in the remaining racks 60 in instrument 10 for outputting all of the test tubes in instrument 10. To return sufficient racks 60 into sample handler 20, the operator may insert empty racks 60 into infeed 80.

Several means are provided to prevent an operator from moving racks 60 in rear area of outfeed 100 from their proper detent positions and away from the registration locations specified in the software which would result in problems with the robotic arm's placement of test tubes into precisely-positioned tube receptacles. A horizontal finger stop 502, ie., a raised horizontal rail, extends horizontally from the bottom of output tray 450 so the operator cannot, by tilting the bottom of a rack toward the back of outfeed 100 during removal of the rack, hit racks in rear area 102. Finger stop 502 rises high enough to block a tilted rack but low enough so that it does not block the movement of rack forward from rear area 102 to front area 570.

Also preventing operator interference are pneumatically-operated clamps 310, 311 mounted to shafts 312, 313 respectively in respective clamping cylinders 314, 315. Air lines supply air to open and close clamping cylinders 314, 315. Whenever tray 450 is moving, and at most other times, shafts 312, 313 are raised above outfeed 100. However, when software in instrument 10 determines that a rack is positioned in the frontmost detent 539 on outfeed 100 as in FIG. 3F and tray 450 is not moving, clamp cylinders 314, 315 will be pneumatically operated to pull clamps 310, 311 down into recesses 115, 116 in tabs 110, 111 on this rack to hold it in this detent 539.

As mentioned above, door panel 45 is also situated above outfeed 100. If door panel 45 is opened by the operator while instrument 10 is operating and the operator inserts a hand above rear area 102, an optical sensor 570, comprising a transmitter mounted to bracket 571 to side wall 510 and receiver mounted to bracket 570 to side wall 511, detects the intrusion and immediately stops instrument 10, including movement of outfeed 100 and the robotic arm, to prevent the operator from being injured by a moving walking beam or robotic arm. Thus, sensor 570 operates as a "light curtain".

Stat Shuttle

Sample handler 20 may also be provided with a stat shuttle 600 mounted parallel to and between infeed 80 and outfeed 100. (FIGS. 1A and 1B) Test tubes and other containers, may be fed into the instrument using the stat shuttle 600 to process these containers on a priority basis, with the instrument interrupting the normal operation of processing containers input via infeed 80. Stat shuttle 600 also enables the feeding of other types of containers, such as reagent and diluent packages, into the instrument on the stat shuttle 600. Stat shuttle 600 may also be used to output containers from the instrument.

Referring to FIG. 9, stat shuttle 600 comprises a linear transport mechanism 610, similar to the linear transport mechanism for cross-feed 95, coupled to a microprocessor-controlled stepper motor 615, such as motor 350, via similar pulleys and drive belts. A platform (not shown) is connected to the linear transport mechanism 610 and an adapter 605, as described in the referenced application entitled Stat Shuttle Adapter and Transport Device, may be mounted to the platform. One of racks 60 may be inserted into adapter 605 to transport test tubes into and out of sample handler 20, either because one or more samples must be analyzed on a high priority or where infeed 80 is broken. Other adapters, such as container-specific adapters like the reagent package and diluent package adapters, may be inserted into adapter 605 to transport containers on stat shuttle 600. As with cross-feed 95, a bar code reader 623 (FIG. 1C) is placed alongside stat-shuttle 600 to read bar code labels on racks 60, adapters, test tubes and other containers and an ultrasonic liquid level sensor 625 is positioned above the path of adapter 605 and is mounted in a bracket 635 adjacent the stat shuttle 600. Due to space constraints, in a preferred embodiment, bar code reader 623 is not positioned directly at containers in stat shuttle 600 but instead bar code reader 623 reads the bar codes as reflected by mirror 627 positioned at a 45 degree angle between the right side and rear of sample handler 20.

Containers, such as test tubes, may be inserted into stat shuttle 600 by an operator in a front area 600a of stat shuttle 600 and stat shuttle 600 transports the containers to a rear area 600b of stat shuttle 600 where a robotic arm may retrieve the containers from preferably predefined registration positions. Similarly, the robotic arm may return the containers to one of the predefined registration positions on stat shuttle 600 to output the containers.

Stat shuttle may also be used in a situation where reader 55 along cross-feed 95 was unable to read the machine-readable code on the test tube or other container or sensor 90 was unable to obtain usable level information from sensor 90. In this situation, the robotic arm may transport the affected container to an awaiting rack in the rear area 600b of stat shuttle 600. Stat shuttle 600 may then output the container to the front area 600a of stat shuttle 600 and then move the container back to rear area 600b. The container thus has another opportunity to pass another reader 623 and sensor 625 to attempt to obtain usable data.

Laboratory Automation

Instrument 10 may be used as a subsystem in a laboratory automation system, such as the Lab Cell system from Bayer Corporation or the automated apparatus described in U.S. Pat. No. 5,623,415, which is assigned to the SmithKline Beecham Corporation. When used in this manner, test tubes are input into instrument from a transport line 700 carrying test tubes adjacent instrument, such as to the left of sample handler 20, rather than from racks 60 in infeed 80. (FIG. 1B). Test tubes in the transport line are individually held in packs which are moved adjacent instrument 10 via diverter gates (not shown) and may be rotated in a specified angular position in the pack. Test tubes are removed from transport line 700 with the robotic arm and transported by robotic arm to instrument 10 for processing.

As with test tubes input into instrument via racks 60, test tubes input into instrument 10 must be identified by a bar code reader 55 and an ultrasonic level sensor 90 before being processed by instrument 10. The test tubes are therefore inserted into a lab automation adapter 710 (FIG. 8A) that is attached to a modified platform (not shown) on cross-feed 95. Adapter 710 comprises an upper rack portion 512 that is similar to racks 60. Upper rack portion 712 has tube receptacles 713 separated by intermediate walls 714, each of tube receptacles 713 having a base 711. Each tube receptacle 713 preferably also has a spring 717, such as a leaf spring, for holding the test tube in the respective tube receptacle.

The adapter 710 has a cover 705, similar to the cover on racks 60. (FIG. 8B) The top of cover 705 is positioned at the same height as the top of one of racks 60 and the base 711 of each tube receptacle 713 is at the same distance from the top of upper rack portion 712 as the base of tube receptacles 63 when one of racks 60 is sitting on track 336. This positions the test tubes to allow bar code reader 55 and ultrasonic liquid level sensor 90 to function properly and positions the test tubes at the proper height for retrieval and placement of the test tubes by a robotic arm on instrument 10. Cover 705 has tabs 110', 111' that are used to provide the reference level for profiling of the rack with sensor 90. For similar reasons of detection and for placing of the test tubes in the same registration positions on cross-feed 95 for retrieval by the robotic arm, there are preferably a similar number of tube receptacles 713 as there are tube receptacles 63 in racks 60 (in the illustrated embodiment, eight tube receptacles).

A front wall 715 of adapter 710 has openings 716 to permit bar code reader 55 to read machine identifiable code such as bar code labels on the test tubes as well as a bar code label 718 on adapter 710. The diverter gates in transport line 700 are used to angularly position each test tube so that the robotic arm inserts test tubes in adapter 710 with the bar code labels positioned in openings 716.

Upper rack portion 712 is connected to a lower rack portion 720 that may form a separate component to which upper rack portion 712 is removably mounted by any conventional means. Lower rack portion 720 has a mounting means 725, such as the illustrated bayonet, to mount adapter 710 to a mount, such as a standard bayonet interlock mount (not shown), on the modified platform, which is preferably substantially the same platform as platform 410 plus the bayonet mount, on cross-feed 95. Thus, unlike racks 60, adapter 710 is snapped in firmly to connector and cannot be pulled up by the robotic arm when test tubes are removed from adapter 710. Mount 735 is positioned between pusher fingers 94a, 94b, which are not used in this mode, and lower rack portion 720 does not come into contact with or utilize the pusher fingers. The modified platform may always be used instead of platform 410 since the modification of the platform does not interfere with the operation of pusher fingers 94a, 94b, When adapter 710 is connected to the modified platform, adapter 710 converts cross-feed 95 to a bidirectional test tube shuttle to transport test tubes removed from transport line along cross-feed 95 in front of bar code reader 55 and under liquid level sensor 90 to the opposite side of cross-feed 95 and may be used to transport test tubes outputted by other modules of instrument 10 back to transport line 700.

The modified platform also has an electrical sensor 740 to detect when the adapter 710 is connected to the modified platform so that software disables the walking beam mechanisms of infeed 80 and outfeed 100.

Before outputting the test tubes back to transport line, the robotic arm may place the test tubes into a holding area 1000 (FIG. 1A) to provide the instrument with an opportunity to perform reflex testing, i.e., to test the sample again if a particular value was obtained in the first test. After the tests are complete, the robotic arm transports and reinserts the test tubes back in the transport line 700. It is preferable to include two robotic arms on instrument 10 where instrument 10 will be used with a laboratory automation system to increase the throughput instrument 10.

One skilled in the art will recognize that the present invention is not limited to the above-described preferred embodiment, which is provided for the purposes of illustration and not limitation. Modifications and variations, in particular, to dimensions of components (e.g., size of tubes and racks), the number of components within a subassembly (e.g., number of racks or tubes in a rack) and to the walking beam mechanisms, may be made to the above-described embodiment without departing from the spirit and scope of the invention.

We claim:

1. An analytical instrument having a sample handler, said sample handler handling a plurality of racks to transport a plurality of containers within said sample handler and a robotic arm to transport said containers within said instrument, said sample handler comprising an infeed into which said racks in which said containers are seated are input, an outfeed to which said racks are output, a cross-feed extending between said infeed and said outfeed, to which said racks are transferred from said infeed, a first device adjacent said cross-feed for detecting a property of at least one of said racks or containers while said racks and containers are on said cross-feed, a stat shuttle, and a second device adjacent said stat shuttle substantially identical to said first device to which said robotic arm may move those of said containers for which said first device failed to detect said property to attempt to detect said property using said second device.

2. The instrument of claim 1, wherein said first and second device are readers for reading machine-readable identification codes on said racks and containers.

3. The instrument of claim 1, wherein said first and second device are ultrasonic liquid level sensors for taking a plurality of level readings of said racks and containers in said racks.

4. A sample handler for transporting a plurality of racks within an instrument each rack having a plurality of containers disposed therein, said sample handler comprising:

an infeed into which said racks are input, said infeed comprising a walking beam mechanism, an outfeed to which said racks are output, a cross-feed extending between said infeed and said outfeed, to which said racks are transferred from said infeed having means to transport at least one of said racks from a first position adjacent said infeed to a second position adjacent said outfeed, and an ultrasonic level sensor positioned above said cross-feed between said first and second positions to take a plurality of level readings of said at least one rack.

* * * * *